(12) United States Patent
Stroefer et al.

(10) Patent No.: US 8,933,262 B2
(45) Date of Patent: Jan. 13, 2015

(54) PROCESS FOR PREPARING POLYISOCYANATES FROM BIOMASS

(75) Inventors: Eckhard Stroefer, Mannheim (DE);
Otto Machhammer, Mannheim (DE);
Stefan Bitterlich, Dirmstein (DE);
Roman Prochazka, Mannheim (DE);
Mario Emmeluth, Bensheim (DE);
Julia Leschinski, Ixelles (BE);
Emmanouil Pantouflas, Weinheim (DE); Dirk Klingler, Mannheim (DE);
Stephan Deuerlein, Ludwigshafen (DE);
Stephan Schunk, Heidelberg (DE);
Jochem Henkelmann, Ludwigshafen (DE); Dieter Stützer, Dudenhofen (DE)

(73) Assignee: BASF SE, Ludwigshafen (DE)

( * ) Notice: Subject to any disclaimer, the term of this patent is extended or adjusted under 35 U.S.C. 154(b) by 170 days.

(21) Appl. No.: 13/479,961

(22) Filed: May 24, 2012

(65) Prior Publication Data

US 2012/0302786 A1 Nov. 29, 2012

Related U.S. Application Data

(60) Provisional application No. 61/489,268, filed on May 24, 2011.

(51) Int. Cl.
*C07C 263/00* (2006.01)
*C07C 263/10* (2006.01)

(52) U.S. Cl.
CPC .................................. *C07C 263/10* (2013.01)
USPC ........................................................ 560/347

(58) Field of Classification Search
None
See application file for complete search history.

(56) References Cited

U.S. PATENT DOCUMENTS

| | | |
|---|---|---|
| 2,057,117 A | 10/1936 | Sandborn et al. |
| 2,739,174 A | 3/1956 | Ross |
| 2,773,911 A | 12/1956 | Dubois et al. |
| 2,849,497 A | 8/1958 | Buchanan |
| 3,375,283 A | 3/1968 | Goheen et al. |
| 3,578,714 A | 5/1971 | Russell |
| 3,775,504 A | 11/1973 | Sampson et al. |
| 4,409,416 A | 10/1983 | Snell et al. |
| 4,420,644 A | 12/1983 | Huibers et al. |
| 5,214,210 A | 5/1993 | Schutz et al. |
| 5,302,763 A | 4/1994 | Quakenbush |
| 5,391,683 A | 2/1995 | Joulak et al. |
| 6,429,338 B1 | 8/2002 | Burdeniuc et al. |
| 6,683,204 B1 | 1/2004 | Stamm et al. |
| 6,833,469 B2 | 12/2004 | Wölfert et al. |
| 7,064,237 B2 | 6/2006 | Zehner et al. |
| 7,112,694 B2 | 9/2006 | Woelfert et al. |
| 7,230,130 B2 | 6/2007 | Ströfer et al. |
| 8,097,751 B2 | 1/2012 | Koch et al. |
| 8,450,541 B2 * | 5/2013 | Seames et al. ................ 585/240 |
| 2004/0068137 A1 | 4/2004 | Herold et al. |
| 2009/0227823 A1 | 9/2009 | Huber et al. |
| 2010/0145117 A1 | 6/2010 | Seames et al. |
| 2011/0137097 A1 | 6/2011 | Tschirschwitz et al. |
| 2011/0144398 A1 | 6/2011 | Mirk et al. |
| 2011/0163258 A1 | 7/2011 | Seeler et al. |
| 2011/0178329 A1 | 7/2011 | Bock et al. |
| 2011/0207961 A1 | 8/2011 | Geissler et al. |
| 2011/0218359 A1 | 9/2011 | Limbach et al. |
| 2011/0268652 A1 * | 11/2011 | Machhammer et al. ... 423/648.1 |
| 2011/0275868 A1 | 11/2011 | Prochazka et al. |
| 2011/0275869 A1 | 11/2011 | Prochazka et al. |
| 2011/0306812 A1 | 12/2011 | Rohde et al. |
| 2011/0313192 A1 | 12/2011 | Rosendahl et al. |
| 2012/0029243 A1 | 2/2012 | Pantouflas et al. |
| 2012/0058463 A1 | 3/2012 | Deuerlein et al. |
| 2012/0071671 A1 | 3/2012 | Karpov et al. |
| 2012/0087851 A1 | 4/2012 | Deuerlein et al. |
| 2012/0101299 A1 | 4/2012 | Schelling et al. |
| 2012/0108843 A1 | 5/2012 | Schelling et al. |
| 2012/0108844 A1 | 5/2012 | Schelling et al. |
| 2012/0132032 A1 | 5/2012 | Domke et al. |
| 2012/0157722 A1 | 6/2012 | Denissen et al. |
| 2012/0165585 A1 | 6/2012 | Schneider et al. |
| 2012/0165588 A1 | 6/2012 | Dehn et al. |
| 2012/0172620 A1 | 7/2012 | Schelling et al. |
| 2012/0172621 A1 | 7/2012 | Mattke et al. |
| 2012/0190537 A1 | 7/2012 | Hannemann et al. |
| 2012/0190538 A1 | 7/2012 | Hannemann et al. |

FOREIGN PATENT DOCUMENTS

| | | |
|---|---|---|
| BE | 724918 | 5/1969 |
| CN | 1854114 A | 11/2006 |
| DE | 1 289 530 | 2/1969 |
| DE | 238 042 A1 | 8/1986 |
| DE | 295 628 A5 | 11/1991 |

(Continued)

OTHER PUBLICATIONS

U.S. Appl. No. 13/502,763, filed Apr. 19, 2012, Bock, et al.
U.S. Appl. No. 13/513,460, filed Jun. 1, 2012, Bock, et al.
U.S. Appl. No. 13/513,595, filed Jun. 4, 2012, Mattke, et al.
U.S. Appl. No. 13/513,752, filed Jun. 4, 2012, Franzke, et al.
U.S. Appl. No. 13/207,266, Leschinski, et al.

(Continued)

*Primary Examiner* — Karl J Puttlitz
(74) *Attorney, Agent, or Firm* — Oblon, Spivak, McClelland, Maier & Neustadt, L.L.P.

(57) ABSTRACT

The present invention relates to a process for preparing polyisocyanates from natural raw material sources, in which a composition comprising low molecular weight aromatics which comprise at least one hydroxy group or at least one alkoxy group per molecule (oxyaromatics) is produced from a biomass material, these oxyaromatics are converted into the corresponding aromatic amines and, optionally after condensation with formaldehyde, reacted further with phosgene to give compounds comprising isocyanate groups.

32 Claims, 1 Drawing Sheet

(56) References Cited

FOREIGN PATENT DOCUMENTS

| | | |
|---|---|---|
| DE | 42 30 099 A1 | 3/1994 |
| DE | 44 28 460 A1 | 2/1996 |
| DE | 44 28 461 A1 | 2/1996 |
| DE | 199 61 973 A1 | 6/2001 |
| DE | 102 23 483 A1 | 3/2003 |
| DE | 103 29 303 A1 | 2/2005 |
| DE | 10 2006 011 497 A1 | 9/2007 |
| EP | 0 184 569 A1 | 6/1986 |
| EP | 0 321 275 A2 | 6/1989 |
| EP | 0 489 211 A1 | 6/1992 |
| EP | 0 593 334 A1 | 4/1994 |
| EP | 0 597 361 A1 | 5/1994 |
| EP | 0 696 573 A1 | 2/1996 |
| EP | 0 748 788 A1 | 12/1996 |
| EP | 0 748 789 A2 | 12/1996 |
| EP | 0 799 817 A1 | 10/1997 |
| EP | 0 903 336 A2 | 3/1999 |
| EP | 0 976 718 A2 | 2/2000 |
| EP | 1 132 347 A2 | 9/2001 |
| EP | 1 270 544 A1 | 1/2003 |
| EP | 1 137 623 B1 | 6/2003 |
| EP | 1 350 787 A1 | 10/2003 |
| EP | 1 403 248 A1 | 3/2004 |
| EP | 1 445 246 A2 | 8/2004 |
| EP | 1 616 857 A1 | 1/2006 |
| EP | 1 509 496 B1 | 12/2006 |
| EP | 1 880 989 A1 | 1/2008 |
| EP | 1 401 802 B1 | 4/2008 |
| EP | 1 797 236 B1 | 6/2011 |
| EP | 1 794 363 B1 | 2/2012 |
| GB | 586732 | 3/1947 |
| WO | WO 96/09350 | 3/1996 |
| WO | WO 99/10450 | 3/1999 |
| WO | WO 01/64333 A2 | 9/2001 |
| WO | WO 03/045900 A1 | 6/2003 |
| WO | WO 2004/056756 A1 | 7/2004 |
| WO | WO 2005/075407 A1 | 8/2005 |
| WO | WO 2006/031175 A1 | 3/2006 |
| WO | WO 2006/038863 A1 | 4/2006 |
| WO | WO 2006/048141 A1 | 5/2006 |
| WO | WO 2006/048171 A1 | 5/2006 |
| WO | WO 2006/066762 A1 | 6/2006 |
| WO | WO 2006/130405 A2 | 12/2006 |
| WO | WO 2007/051851 A1 | 5/2007 |
| WO | WO 2007/051852 A2 | 5/2007 |
| WO | WO 2007/051855 A2 | 5/2007 |
| WO | WO 2007/051856 A1 | 5/2007 |
| WO | WO 2008/006775 A1 | 1/2008 |
| WO | WO 2008/027699 A2 | 3/2008 |
| WO | WO 2008/049783 A1 | 5/2008 |
| WO | WO 2008/079072 A1 | 7/2008 |
| WO | WO 2008/086922 A1 | 7/2008 |
| WO | WO 2008/135581 A1 | 11/2008 |
| WO | WO 2008/135582 A1 | 11/2008 |
| WO | WO 2008/148807 A1 | 12/2008 |
| WO | WO 2009/108599 A2 | 9/2009 |
| WO | WO 2009/108601 A2 | 9/2009 |
| WO | 2009/135843 A1 | 11/2009 |
| WO | WO 2010/026244 A1 | 3/2010 |
| WO | WO 2010/062390 A2 | 6/2010 |
| WO | WO 2010/136551 A2 | 12/2010 |
| WO | WO 2010/149544 A2 | 12/2010 |
| WO | WO 2010/149701 A1 | 12/2010 |
| WO | WO 2011/006807 A2 | 1/2011 |
| WO | WO 2011/006970 A1 | 1/2011 |
| WO | WO 2011/015541 A1 | 2/2011 |
| WO | WO 2011/023638 A1 | 3/2011 |
| WO | WO 2011/026744 A2 | 3/2011 |
| WO | WO 2011/036062 A2 | 3/2011 |
| WO | WO 2011/051314 A1 | 5/2011 |
| WO | WO 2011/067242 A1 | 6/2011 |
| WO | WO 2011/067278 A1 | 6/2011 |
| WO | WO 2011/067369 A1 | 6/2011 |
| WO | WO 2011/069933 A2 | 6/2011 |
| WO | WO 2011/069957 A1 | 6/2011 |
| WO | WO 2011/083054 A1 | 7/2011 |
| WO | WO 2011/089098 A1 | 7/2011 |
| WO | WO 2011/107559 A2 | 9/2011 |
| WO | WO 2011/138355 A2 | 11/2011 |
| WO | WO 2011/138356 A1 | 11/2011 |
| WO | WO 2011/138357 A1 | 11/2011 |
| WO | WO 2011/157674 A1 | 12/2011 |
| WO | WO 2011/161029 A1 | 12/2011 |
| WO | WO 2012/013735 A1 | 2/2012 |
| WO | WO 2012/025393 A1 | 3/2012 |
| WO | WO 2012/028701 A2 | 3/2012 |
| WO | WO 2012/049611 A1 | 4/2012 |
| WO | WO 2012/072615 A1 | 6/2012 |
| WO | WO 2012/084673 A1 | 6/2012 |
| WO | WO 2012/101566 A1 | 8/2012 |
| WO | WO 2012/101567 A2 | 8/2012 |
| WO | WO 2012/104292 A1 | 8/2012 |
| WO | WO 2012/117099 A1 | 9/2012 |
| WO | WO 2012/140065 A1 | 10/2012 |

OTHER PUBLICATIONS

U.S. Appl. No. 13/409,657, filed Mar. 1, 2012, Leschinski, et al.
U.S. Appl. No. 13/434,176, filed Mar. 29, 2012, Deuerlein, et al.
Michael Stöcker, "Bio- und BTL-Kraftstoffe in der Bioraffinerie: katalytische Umwandlung Lignocellulose-reicher Biomasse mit porösen Stoffen", Angewandte Chemie, vol. 120, 2008, pp. 9340-9351.
George W. Huber, et al., "Synthesis of Transportation Fuels from Biomass: Chemistry, Catalysts, and Engineering", Chemical Reviews, vol. 106, No. 9, 2006, pp. 4044-4098.
U.S. Appl. No. 14/069,759, filed Nov. 1, 2013, Mueller, et al.
U.S. Appl. No. 13/983,089, filed Aug. 1, 2013, Rieger, et al.
English translation of the International Search Report issued Aug. 24, 2012, in PCT/EP2012/059525.
English translation of the International Preliminary Report on Patentability and Written Opinion issued Dec. 5, 2013, in PCT/EP2012/059525 filed May 23, 2012.
Office Action issued Aug. 19, 2014, in EP patent Application No. 12723181.9-1454/2714650.

* cited by examiner

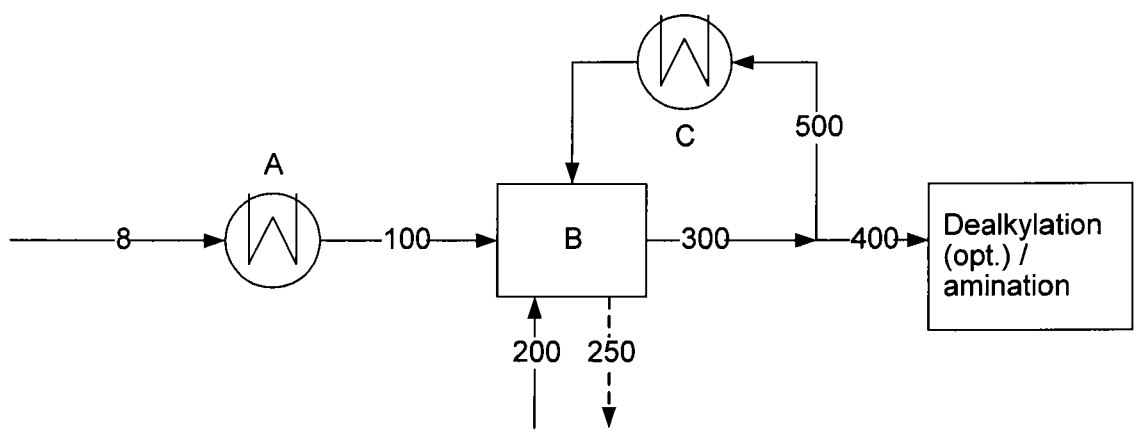

PROCESS FOR PREPARING POLYISOCYANATES FROM BIOMASS

BACKGROUND TO THE INVENTION

The present invention relates to a process for preparing polyisocyanates from natural raw material sources, in which a composition comprising low molecular weight aromatics which comprise at least one hydroxy group or at least one alkoxy group per molecule (oxyaromatics) is produced from a biomass material, these oxyaromatics are converted into the corresponding aromatic amines and, optionally after condensation with formaldehyde, reacted further with phosgene to give compounds comprising isocyanate groups.

PRIOR ART

Polyisocyanates (in accordance with general practice, the compounds having more than 2 NCO groups per molecule will hereinafter sometimes also be referred to as "diisocyanates") are valuable raw materials for the production of polyurethanes. Polyurethanes are the class of plastics having the widest range of applications. Accordingly, the worldwide markets for polyisocyanates and polyurethanes have been displaying high growth rates for years. The most important diisocyanates are MDI (methyl-enedi(phenyl isocyanate)) and TDI (tolylene diisocyanate).

MDI is, firstly, marketed as a mixture of oligomers and isomers which is known as polymeric MDI (PMDI, polymethylenepolyphenylene polyisocyanate). Secondly, MDI is marketed in the form of the lowest oligomer, namely 2-ring MDI, which comprises only two aromatic rings in the molecule and is also referred to as monomeric MDI (MMDI). MMDI is offered for sale either in pure isomer form or as a mixture of various isomers. The oligomer and isomer composition of PMDI is determined by the production process, the operating conditions thereof and the way in which the process is carried out. PMDI is thus a typical example of a product which can be best characterized by its production process. The MMDI can be separated off from the crude product of the process (the crude MDI mixture) by a separation step. On an industrial scale, this separation step is generally a distillation or crystallization.

The process for the preparation of TDI likewise firstly gives a crude TDI mixture which comprises predominantly isomers of TDI and oligomers which are crosslinked via urea and diisocyanate groups. The composition of the oligomers is likewise determined by the production process. The pure isomers or particular isomer mixtures can be obtained from the crude TDI mixture by separation, which generally comprises a distillative separation step.

As intermediate for the preparation of MDI, the corresponding MDA (methylene-di(phenylamine)) can be condensed with formaldehyde in the presence of an acid catalyst by conventional processes. This process can be carried out either continuously or batchwise (e.g. DD 295628 and DD 238042). Furthermore, it is known that diisocyanates can be prepared from corresponding amines and phosgene. The reaction is, depending on the type of amines, carried out either in the gas phase or in the liquid phase, either batchwise or continuously. The continuous preparation of organic diisocyanates by means of reactions of primary organic amines and phosgene has been described many times and is practiced on an industrial scale.

Modern-day industrial syntheses of the abovementioned diisocyanates are virtually exclusively carried out continuously. In general, the continuous embodiment of the process comprises a plurality of stages. In the first stage of the phosgenation, the amine is reacted with phosgene to form the corresponding carbamoyl chloride and hydrogen chloride and amine hydrochlorides. The primary reaction between amines and phosgene is very fast and exothermic. To minimize the formation of by-products and solids, amine and phosgene, both optionally dissolved in an organic solvent, can, for example, be mixed rapidly. The next stage of the phosgenation comprises both the decomposition of the carbamoyl chloride into the desired diisocyanate and hydrogen chloride and also the phosgenation of the amine hydrochloride to the carbamoyl chloride.

Liquid-phase phosgenations are, for example, described in EP-A-1 616 857, WO 2004/056756, WO 2006/130405, EP-A-1 509 496, EP-A-1 270 544 and DE-A-199 61 973.

To avoid the formation of undesirable intermediates of the amine hydrochlorides, the phosgenation can also be carried out as a gas-phase phosgenation at high temperatures. Such processes are described by way of example in EP-A-593 334, WO 2003/045900, WO 2008/086922 and WO 2008/006775 (aerosol phosgenation).

Furthermore, the phosgenation can be carried out in supercritical solvents (WO 2008/049783). It is also possible to use the isocyanates themselves (EP-A-1 401 802, U.S. Pat. No. 6,683,204) or ionic liquids (WO 06048141, WO 2006/048171) as solvents.

An important problem to be solved is the inexpensive and long-term provision of suitable amines which make up from 40 to 80% of the production costs of the polyisocyanates and whose availability on the world market is limited. This problem is particularly significant for the provision of aromatic amines.

In the prior art, aromatic amines are conventionally prepared from the corresponding aromatics, e.g. benzene or toluene, by means of a nitration step with subsequent hydrogenation of the nitro group to form the corresponding amine. A large number of batch and continuous processes are known for the preparation of nitroaromatics. The nitrating agent is generally either a mixture of nitric acid and sulfuric acid or nitric acid alone. After the aromatic compound has been functionalized by nitration, it has to be hydrogenated in order to obtain the corresponding amine. The hydrogenation is generally carried out in the presence of a catalyst, with water being obtained as by-product. It can be carried out industrially in a wide variety of industrial embodiments such as fluidized beds or fixed beds or in a liquid or gaseous phase.

The preparation of polyisocyanates according to the prior art thus has the following technical disadvantages:

Both the nitration step and the hydrogenation step produce wastewater which requires special treatment.

Since nitrocompounds are energy-rich materials having very high decomposition energies (>1000 J/g), the processes make elaborate safety measures necessary.

The functionalization of the aromatic base molecule to provide the amine for the preparation of TDI or MDI requires a complicated multistage process.

There is therefore a need for an alternative way of providing suitable amines for the preparation of polyisocyanates.

The large amounts of biomass produced continuously by nature have hitherto been used to only a small extent as renewable raw material for utilization as material or for the generation of energy. To conserve raw material resources, it is necessary to have processes which make the replacement of fossil raw materials by biomass starting materials possible. To achieve a high efficiency, ideally complete utilization of the biomass material provided is sought.

It is known that streams from various digestion processes for materials comprising lignin or lignocellulose can be subjected to an after-treatment to obtain materials of value.

U.S. Pat. No. 2,057,117 describes a process for preparing vanillin, in which a starting material selected from lignocellulose, a crude lignin extract and lignosulfonic acid is heated with an aqueous alkali metal hydroxide solution under superatmospheric pressure and the reaction mixture obtained is admixed with sulfuric acid in order to precipitate organic constituents and convert the vanillin into a soluble form.

WO 99/10450 describes a process for converting lignin into a hydrocarbon fuel. Here, lignin is subjected to a base-catalyzed depolymerization and subsequently to hydroprocessing. This hydroprocessing comprises a hydrodeoxygenation and mild hydrocracking. The latter is carried out under conditions under which partial hydrogenation of the aromatic rings occurs.

WO 2008/027699 A2 describes a process in which lignin originating from pyrolysis of biomass is, after removal of water-soluble constituents, decarboxylated and hydrodeoxygenated and the organic products from this process step are subsequently subjected to hydrocracking.

WO 2010/026244 describes an integrated process for producing cellulose and at least one low molecular weight material of value, in which
a) a lignocellulose-comprising starting material is provided and subjected to digestion with a treatment medium,
b) a cellulose-enriched fraction and at least one cellulose-depleted fraction are isolated from the digested material, with the cellulose-depleted fraction comprising at least part of the treatment medium from step a),
c) the cellulose-depleted fraction is subjected to a treatment to give at least one low molecular weight material of value and
d) the material/materials of value is/are isolated from the treatment product obtained in step c).

WO 2009/108601 describes a process for producing a starting material for biorefinery processes to produce a biofuel from a lignin-comprising starting material. Here, lignin from a black liquor of the pulping process or the black liquor itself is subjected to hydroprocessing in the presence of a hydrogen-comprising gas and a catalyst on an amorphous or crystalline oxidic support.

WO 2009/108599 has a disclosure content comparable to WO 2009/108601, with the focus on paper production.

In Angew. Chem. 2008, 120, 9340-9351, M. Stöcker describes the catalytic conversion of lignocellulose-rich biomass to obtain BTL (biomass-to-liquid) fuels in biorefineries.

US 2009/0227823 describes a process for producing at least one liquid hydrocarbon product from a solid hydrocarbon starting material (e.g. a lignocellulose material), in which the starting material is subjected to catalytic pyrolysis and the pyrolysis products are subjected to a subsequent catalyzed reaction to give liquid products.

In Chem. Rev. 2006, 106, 4044-4098, G. W. Huber et al. describe the synthesis of fuels from biomass. According to this document, lignocellulose materials can in principle be converted into liquid fuels via three routes which differ in terms of their initial step: gasification to form synthesis gas, pyrolysis to bio-oil, hydrolysis to give sugars and lignin. The bio-oils obtained in the pyrolysis can subsequently be subjected to hydrodeoxygenation in the presence of hydrogen or to steam reforming.

The unpublished European patent applications 10162255.3, 10162256.1 and 10162259.5 describe the preparation of organic materials of value from the digestion of lignocellulose-comprising starting materials. The unpublished European patent application 10171278.4 describes a composition (composite) comprising lignin and at least one catalyst dispersed in the composition, a process for producing such a catalyst- and lignin-comprising composition and the use thereof for preparing an aromatics composition.

None of the abovementioned documents relating to a biorefinery gives any suggestion of using a biomass starting material for the integrated preparation of aromatic polyisocyanates from the corresponding aromatic amines and of further products of value.

The problem of providing suitable amines for the preparation of polyisocyanates has surprisingly been able to be solved by utilizing a by-product of the work-up of a biological basic product to give a product of value in order to provide aromatic amines. This is specifically the reaction of lignin which is obtained in the processing of lignocellulose-comprising materials, e.g. wood or bagasse, for example in paper production, and from which aromatic amines which are particularly advantageous for the preparation of polyisocyanates can be obtained by the process of the invention.

A significant aspect of the present invention is the economically and ecologically improved provision of aromatic amines by utilization of the functionalization of aromatic compounds as brought about by nature.

SUMMARY OF THE INVENTION

It has surprisingly been found that an advantageous preparation of polyisocyanates having aromatic rings from a biomass starting material is possible.

The invention therefore firstly provides a process for preparing polyisocyanates, in which a biomass starting material is used for preparing a composition of aromatic amines having a $C^{14}$ to $C^{12}$ isotope ratio in the range from $0.5 \times 10^{-12}$ to $5 \times 10^{-12}$ and the composition of aromatic amines is subjected to phosgenation.

As regards suitable and preferred embodiments of the phosgenation, the information given below for step g) is fully incorporated by reference.

The biomass starting material for preparing the composition of aromatic amines is preferably subjected to at least one reaction which comprises a decomposition to give an aromatics composition comprising aromatics which have at least one hydroxy group and/or at least one alkoxy group per molecule ("oxyaromatics composition") and the oxyaromatics composition is subjected to amination.

The oxyaromatics composition preferably comprises, based on the total weight, at least 75% by weight, particularly preferably at least 90% by weight, in particular at least 95% by weight, of monocyclic aromatics.

The invention further provides a process for preparing polyisocyanates, in which
   a biomass starting material is subjected to a reaction comprising a decomposition to give an aromatics composition comprising aromatics which have at least one hydroxy group and/or at least one alkoxy group per molecule ("oxyaromatics composition"),
   the oxyaromatics composition is subjected to amination,
   the amination product is optionally subjected to condensation with a formaldehyde source,
   the amination product or (if the amination product is subjected to condensation with a formaldehyde source) the product of the condensation with a formaldehyde source is subjected to phosgenation.

As regards suitable and preferred embodiments for the decomposition of the biomass starting material, the information given below for step b) is fully incorporated by reference.

As regards further reaction and/or work-up steps to which the (digested) biomass starting material can be subjected, the information given below for steps c) and d) is fully incorporated by reference.

As regards suitable and preferred embodiments of the amination, the information given below for step e) is fully incorporated by reference. Ammonia is preferably used for the amination.

As regards suitable and preferred embodiments of the condensation with a formaldehyde source, the information given below for step f) is fully incorporated by reference.

As regards suitable and preferred embodiments of the phosgenation, the information given below for step g) is fully incorporated by reference.

The invention further provides a process for preparing polyisocyanates, in which
a) a biomass starting material is provided,
b) the biomass starting material is subjected to decomposition,
c) the decomposed material obtained in step b) is optionally separated into at least one aromatics-enriched fraction C1) and at least one aromatics-depleted fraction C2),
d) the decomposition product from step b) or the aromatics-enriched fraction C1) from step c) is optionally fed into a dealkylation zone and reacted in the presence of hydrogen and/or water vapor,
a discharge is taken from the dealkylation zone and
the discharge from the dealkylation zone is optionally subjected to a separation to give at least one stream D1) enriched in dealkylated aromatics and at least one stream D2) enriched in more volatile components,
e) the decomposition product from step b) or the aromatics-enriched fraction C1) from step c) or the discharge from the dealkylation zone in step d) or the stream D1) enriched in dealkylated aromatics is subjected to amination by reaction with an ammonia source in an amination zone,
f) the amination product from step e) is optionally subjected to condensation with a formaldehyde source,
g) the amination product from step e) or the product of the condensation with a formaldehyde source from f) is subjected to phosgenation.

The invention further provides a polyisocyanate composition in which the $C^{14}$ to $C^{12}$ isotope ratio is in the range from $0.4 \times 10^{-12}$ to $4.5 \times 10^{-12}$.

The invention further provides a polyisocyanate composition which can be obtained by a process as described above and below.

The polyisocyanate composition of the invention preferably has an NCO number of at least 30.

BRIEF DESCRIPTION OF THE SEVERAL VIEWS OF THE DRAWINGS

FIG. 1 is a schematic of a preferred embodiment for evaporation.

DESCRIPTION OF THE INVENTION

For the purposes of the present patent application, the term "biomass" refers to a plant material of nonfossil origin. Biomass includes plants and plant parts which have died off, e.g. dead wood, straw, leaves, etc. The term biomass also comprises products in which a plant material of nonfossil origin has been subjected to a chemical and/or physical treatment. Such products include in particular the products from the digestion and fractionation of lignocellulose, e.g. lignin. Biomass specifically does not include coal, petroleum, natural gas, peat and upgrading products thereof, e.g. coke.

For the purposes of the invention, the expression "oxyaromatics" refers to aromatics having at least one hydroxy group and/or at least one alkoxy group per molecule. Accordingly, an "oxyaromatics composition" is a composition comprising oxyaromatics. Preferred oxyaromatics are monocyclic aromatics or compositions having a high content of monocyclic aromatics. The oxyaromatics composition used in the process of the invention preferably comprises, based on the total weight, at least 75% by weight, preferably at least 90% by weight, in particular at least 95% by weight, of monocyclic aromatics.

The monocyclic oxyaromatics are preferably selected from among compounds of the general formula (I)

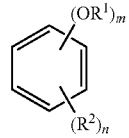

where
the radicals $R^1$ are each, independently of one another, hydrogen or $C_1$-$C_6$-alkyl,
the radicals $R^2$ are selected independently from among $C_1$-$C_6$-alkyl, $C_1$-$C_6$-hydroxyalkyl, formyl, $C_2$-$C_6$-acyl, $C_1$-$C_6$-alkoxycarbonyl and $C_1$-$C_6$-alkylcarbonyloxy,
m is 1, 2 or 3,
n is 0, 1, 2, 3 or 4 and
the sum of m and n is an integer from 1 to 6.

The process of the invention makes it possible, in particular, to provide an oxyaromatics composition comprising monomeric oxyaromatics selected from among phenol, phenol ethers, cresols, xylenols, guaiacols, veratrols, resorcinol, catechol, hydroquinone and mixtures thereof.

In a specific embodiment, the process of the invention comprises provision of an oxyaromatics composition having a high content of monocyclic aromatics from a biomass starting material. For the purposes of the invention, monocyclic aromatics are also referred to as "monomeric aromatics". Polycyclic aromatics having from 2 to 15 aromatic rings are also referred to as "oligomeric aromatics".

If a biomass starting material is subjected to at least one decomposition for preparing the composition of aromatic amines in the process of the invention, an aromatics composition comprising, based on the total weight, at least 1% by weight, particularly preferably at least 2% by weight, of monocyclic oxyaromatics is obtained as primary decomposition product. The proportion of monocyclic oxyaromatics can be significantly increased by means of further reaction and/or work-up steps as described below. The additional components obtained here can advantageously be recycled to the process of the invention or worked up to give a further product of value or utilized for energy generation.

In a specific embodiment, the reaction of the biomass starting material to provide the oxyaromatics composition comprises at least one dealkylation. The dealkylation products obtained in this way have a significantly higher content of monocyclic dealkylated aromatics than the initial aromatics composition. Such an oxyaromatics composition is particularly advantageous for the further conversion into polyisocyanates.

For the purposes of the invention, the term "dealkylation" refers to a reaction of the substituted and/or polycyclic aromatic compounds comprised in an aromatics composition in the presence of hydrogen and/or water vapor, with these being at least partly transformed in such a way that substituents are replaced by hydrogen and/or compounds comprising a plurality of aromatic rings are cleaved to form compounds having a smaller number of rings. The substituents replaced by hydrogen are selected from among alkyl groups, hydroxy groups, alkoxy groups, aryloxy groups, etc. For the purposes of the invention, the term "dealkylation" also comprises other reactions associated with a decrease in molecular weight, e.g. dehydroxylation, dealkoxylation or aromatics cleavage. Here, the term aromatics cleavage refers to a reaction in which the number of aromatic rings per molecule is essentially reduced without the aromatic rings themselves being destroyed. However, the dealkylated oxyaromatics obtained by dealkylation always have, according to the invention, at least one hydroxy group and/or at least one alkoxy group per molecule.

Provision of a Biomass Starting Material (Step a)

A lignin-comprising material is preferably provided as biomass starting material in step a) of the process of the invention.

Suitable lignin-comprising starting materials are pure lignin and lignin-comprising compositions. Here, the lignin content of the compositions is not critical within a wide range; only at lignin contents which are too low does the process no longer operate economically.

Preference is given to a lignin-comprising starting material which comprises at least 10% by weight, preferably at least 15% by weight, based on the dry mass of the material, of lignin being provided in step a). Lignin-comprising compositions comprising from 10 to 100% by weight, particularly preferably from 15 to 95% by weight, based on the dry mass of the material, of lignin are preferred. For the purposes of the present invention, the term dry mass is used in the sense of the standard ISO 11465.

Lignocellulose-comprising materials are also suitable for providing a lignin-comprising starting material for use in the process of the invention. Lignocellulose forms the structural skeleton of the cell wall of plants and comprises lignin, hemicelluloses and cellulose as main constituents. Further constituents of the cell wall of plants and thus lignocellulose-comprising materials obtained therefrom are, for example, silicates, extractable low molecular weight organic compounds (known as extractables, e.g. terpenes, resins, fats), polymers such as proteins, nucleic acids and vegetable gum (known as exudate), etc.

Lignin is a biopolymer whose basic unit is essentially phenylpropane which can, depending on the natural source, be substituted by one or more methoxy groups on the phenyl rings and with a hydroxy group on the propyl units. Typical structural units of lignin are therefore p-hydroxyphenylpropane, guaiacylpropane and syringylpropane which are joined to one another by means of ether bonds and carbon-carbon bonds.

Both lignocellulose-comprising materials which are used without further chemical treatment in their natural composition, e.g. wood or straw, and lignin-comprising streams from the processing of lignocellulose, e.g. from processes for producing cellulose (pulp processes) are suitable as biomass starting material for the process of the invention.

The lignocellulose materials which can be used according to the invention can be obtained, for example, from wood and plant fibers as starting material. Preferred lignocellulose materials are those composed of wood and residues from the wood-processing industry. They include, for example, the various types of wood, i.e. wood from broadleaved trees such as maple, beech, pear tree, oak, alder, ash, eucalyptus, common beech, cherry tree, lime, nut tree, poplar, willow, etc., and wood from conifers such as Douglas fir, spruce, yew, hemlock, pine, larch, fir, cedar, etc. Wood can not only be classified into broadleaved tree wood and conifer wood but also into "hardwoods" and "softwoods", which is not synonymous with the terms broadleaved tree wood and conifer wood, respectively. In contrast to hardwood, the term softwood refers to lighter wood (i.e. wood having a kiln-dried density below 0.55 g/cm$^3$, for example willow, poplar, lime and virtually all conifer timbers). All hardwoods and all softwoods are in principle suitable for use in the process of the invention. The wood used in the process of the invention can also be present in manufactured form, i.e. in the form of pellets. Suitable residues from the wood-processing industry are wood offcuts and also sawdust, parquetry grinding dust, etc. Further suitable lignocellulose materials are natural fibrous materials such as flax, hemp, sisal, jute, straw, coconut fibers, switchgrass (*Panicum virgatum*) and other natural fibers. Suitable lignocellulose materials are also obtained as residue in agriculture, e.g. in the harvesting of cereal (wheat straw, maize straw, etc.), maize, sugarcane (bagasse), etc. Suitable lignocellulose materials are also obtained as residue in forestry, e.g. in the form of branches, bark, woodchips, etc. Another good source of lignocellulose materials is short rotation crops which make high biomass production on a relatively small area possible.

Preference is given to providing a lignin-comprising stream from the digestion of a lignocellulose material for the production of cellulose (pulp), preferably a black liquor, in particular a black liquor from the Kraft digestion (sulfate digestion), as biomass starting material in step a).

In a preferred embodiment, the biomass starting material is provided by subjecting a lignocellulose-comprising material to digestion and isolating a cellulose-enriched fraction and a lignin-enriched (and simultaneously cellulose-depleted) fraction from the digested material. The latter then serves, optionally after a further work-up, as biomass starting material for the process of the invention. In this embodiment, a lignocellulose-comprising material is thus subjected to a first decomposition in step a) of the process of the invention, a lignin-enriched material is isolated therefrom and this is subsequently subjected to a second decomposition in step b).

Processes for digesting lignocellulose-comprising materials in order to produce cellulose are known in principle. Lignin-comprising streams from all the digestion processes known to those skilled in the art are suitable in principle for use as biomass starting material. These processes can basically be classified according to the treatment medium used into aqueous-alkaline processes, aqueous-acidic processes and organic processes. An overview of these processes and the digestion conditions may be found, for example, in WO 2010/026244.

The treatment medium used for digesting the lignocellulose-comprising materials is capable of solubilizing at least part of the lignin. The cellulose comprised in the lignocellulose-comprising material, on the other hand, is generally not solubilized in the treatment medium or solubilized to only a small extent. A cellulose-enriched fraction is then preferably separated off by filtration or centrifugation.

Preference is given to isolating a lignin-comprising (cellulose-depleted) fraction which in addition to lignin comprises at least one further component selected, for example, from among hemicellulose, cellulose, degradation products of the abovementioned components, digestion chemicals and mixtures thereof from the digested material.

In many cases, it is not critical for the decomposition in step b) if a lignin-comprising starting material which comprises at least one further component in addition to lignin is used as biomass starting material.

If a lignin-comprising fraction which comprises at least one further component in addition to lignin is used for providing the lignin-comprising starting material, at least part of the compounds other than lignin can be removed before the decomposition in step b). The components removed from the lignin-comprising fraction (organic components and/or inorganic process chemicals) are preferably passed to a further work-up and/or thermal utilization, preferably in the process for cellulose production from which the lignin-comprising fraction was obtained.

To remove at least part of the compounds other than lignin, the pH of the lignin-comprising fraction can firstly be set to a suitable value. Lignin-comprising fractions from aqueous-alkaline processes (e.g. the Kraft process) can be admixed with an acid to adjust the pH. Suitable acids are, for example, $CO_2$, mineral acids such as hydrochloric acid, sulfuric acid and phosphoric acid. $CO_2$ (or the carbonic acid resulting therefrom on reaction with water) is particularly preferred as acid. Preference is given to using $CO_2$ from an offgas stream of the process of the invention or of a pulp process coupled with the process of the invention. For example, the offgas from a black liquor combustion (recovery boiler) or a lime kiln is suitable. The offgas can either be introduced directly into the lignin-comprising fraction or be introduced after the other components have been separated off (e.g. by means of a scrubbing process such as a Benfield scrub). The carbonates and/or hydrogencarbonates formed by addition of $CO_2$ can generally be recirculated in a simple way to the coupled pulp process, e.g. to a black liquor taken off before lignin recovery. The use of $CO_2$ for adjusting the pH of the lignin-comprising fraction is thus associated with lower costs than when other acids are used and also generally makes good integration into a pulp process possible.

Lignin-comprising fractions from aqueous-acidic processes can be admixed with a base to adjust the pH. Suitable bases are, for example, alkali metal bases such as sodium hydroxide or potassium hydroxide, alkali metal carbonates such as sodium carbonate or potassium carbonate, alkali metal hydrogencarbonates such as sodium hydrogencarbonate or potassium hydrogencarbonate and alkaline earth metal bases such as calcium hydroxide, calcium oxide, magnesium hydroxide or magnesium carbonate, and also ammonia or amines.

In step a), the removal of at least part of the compounds other than lignin from the lignin-comprising fraction is preferably effected by filtration, centrifugation, extraction, precipitation, distillation, stripping or a combination thereof. A person skilled in the art can control the composition of the lignin-comprising fraction and thus of the lignin-comprising starting material for the decomposition in step b) via the separation process. The at least partial removal of the components other than lignin can be carried out in one or more stages. Customary filtration processes are, for example, cake filtration and deep-bed filtration (e.g. as described in A. Rushton, A. S. Ward, R. G. Holdich: Solid-Liquid Filtration and Separation Technology, VCH Verlagsgesellschaft, Weinheim 1996, pages 177ff., K. J. Ives, in A. Rushton (editor): Mathematical Models and Design Methods in Solid-Liquid Separation, NATO ASI Series E No. 88, Martinus Nijhoff, Dordrecht 1985, pages 90ff.) and crossflow filtrations (e.g. as described in J. Altmann, S. Ripperger, J. Membrane Sci. 124 (1997), pages 119-128). Customary centrifugation process are described, for example, in G. Hultsch, H. Wilkesmann, "Filtering Centrifuges," in D. B. Purchas, Solid-Liquid Separation, Upland Press, Croydon 1977, pages 493-559; and in H. Trawinski, Die äquivalente Klärfläche von Zentrifugen, Chem. Ztg. 83 (1959), pages 606-612. The extraction can, for example, be carried out using a solvent which is immiscible with the treatment medium from pulp production or at least one solvent having a miscibility gap in which lignin and optionally further desired components are soluble in a sufficient amount. The removal of components which can be vaporized without decomposition from the lignin-comprising fraction can be carried out by conventional distillation processes known to those skilled in the art. Suitable apparatuses for work-up by distillation comprise distillation columns such as tray columns which can be equipped with bubble caps, sieve plates, sieve trays, ordered packing, random packing elements, valves, side offtakes, etc., evaporators such as thin film evaporators, falling film evaporators, forced circulation evaporators, Sambay evaporators, etc., and combinations thereof.

In a specific embodiment, a lignin-comprising stream from the digestion of a lignocellulose material which still comprises at least part of the liquid treatment medium from the digestion is used to provide the lignin-comprising starting material in step a). The lignin-comprising stream is then preferably subjected to precipitation of a lignin-comprising fraction, followed by partial or complete removal of the liquid components to provide the lignin-comprising starting material for the decomposition in step b).

The lignin-comprising starting material is preferably provided in a process for producing cellulose (pulp) into which the production according to the invention of synthesis gas and at least one organic liquid or liquefiable material of value is integrated.

In a specific embodiment, the removal of at least part of the liquid compounds is then carried out within the process for producing pulp. Thus, for example, a black liquor which is taken off before or during the individual evaporation steps of the parent pulp process can be used for providing the lignin-comprising starting material.

Preference is given to using a lignin-comprising stream from the digestion of a lignocellulose material by means of an alkaline treatment medium to provide the biomass starting material in step a). Particular preference is given to using a black liquor, in particular a black liquor from sulfate digestion (Kraft digestion). To provide a lignin-comprising material, a black liquor from Kraft digestion can firstly be acidified to precipitate at least part of the lignin present and the precipitated lignin can subsequently be isolated. The abovementioned acids are suitable for acidification. In particular, $CO_2$ is used. The pH of the black liquor is preferably reduced to a value of not more than 10.5. The precipitated lignin is preferably isolated by a filtration process. Suitable filtration processes are those mentioned above. If desired, the isolated lignin can be subjected to at least one further work-up step. Such steps include, for example, a further purification, preferably a scrub using a suitable scrubbing medium. Suitable scrubbing media are, for example, mineral acids such as sulfuric acid, preferably in aqueous solution. In a specific embodiment, a black liquor from Kraft digestion is firstly acidified to precipitate at least part of the lignin present by means of $CO_2$, the precipitated lignin is subsequently isolated by filtration and the filtrate is subjected to scrubbing with sulfuric acid in order to prepare a lignin-comprising material.

One process for isolating lignin from a black liquor by precipitation using $CO_2$ is described in WO 2008/079072, which is hereby incorporated by reference. Another particularly suitable process is the lignoboost process which is described in WO 2006/038863 (EP 1797236 A1) and WO 2006/031175 (EP 1794363 A1), which is likewise incorporated by reference.

Decomposition (Step b)

In step b) of the process of the invention, the biomass starting material is subjected to decomposition to give a decomposition product comprising components whose average molecular weight is significantly below the average molecular weight of the components comprised in the biomass starting material.

In a specific embodiment, a lignin-comprising starting material is used for the decomposition in step b). In this embodiment, the decomposition product obtained in step b) predominantly comprises components having a molecular weight of not more than 500 g/mol, particularly preferably not more than 400 g/mol, in particular not more than 300 g/mol.

The decomposition in step b) can in principle be carried out according to two variants, which are described in detail below. The first variant comprises a pyrolysis and accordingly leads to a pyrolysis product. The second variant comprises a reaction in the presence of a liquid decomposition medium and accordingly leads to a product of liquid decomposition.

$1^{st}$ Variant: Pyrolysis

In a first variant of the process of the invention, the biomass starting material, especially the lignin-comprising starting material, is subjected to pyrolysis in step b). For the purposes of the invention, pyrolysis is a thermal treatment of the biomass starting material, with molecular oxygen being introduced only in a small amount, if at all. For the present purposes, a small amount is an amount which is significantly smaller than the amount necessary for complete oxidation of the carbon comprised in the biomass starting material to $CO_2$. The amount of molecular oxygen introduced in the pyrolysis is preferably at least 50 mol %, particularly preferably at least 75 mol %, in particular at least 90 mol %, below the amount necessary for complete oxidation of the carbon comprised in the biomass starting material to $CO_2$. The pyrolysis generally occurs endothermically. In this variant of the process of the invention, the decomposition product is at least partly obtained in gaseous form.

The pyrolysis can be carried out batchwise or continuously. Continuous pyrolysis is preferred.

The pyrolysis is carried out in at least one pyrolysis zone. The biomass starting material, especially the lignin-comprising starting material, can be introduced into a pyrolysis zone by means of suitable transport devices, e.g. screw conveyors or pneumatic transport.

For the pyrolysis, the biomass starting material, especially the lignin-comprising starting material, is preferably introduced in predominantly solid form. For the purposes of the invention, predominantly solid form means that the starting material used for the pyrolysis has a liquid content under standard conditions (20° C., 1013 mbar) of not more than 70% by weight, particularly preferably not more than 50% by weight, based on the total weight of the starting material. The biomass starting material, especially the lignin-comprising starting material, is then used, for example, as moist or pre-dried solid for the pyrolysis.

The pyrolysis zone can be configured in various embodiments, e.g. as rotary tube furnace or fluidized bed. Both static and circulating fluidized beds are suitable. When the pyrolysis zone is configured as a fluidized bed, a fluidizing gas (preferably steam or a gas mixture from one of the subsequent process steps) is used and a particulate additional material which is inert under the prevailing conditions is introduced as material to be fluidized. Silica sand is particularly suitable as additional material. Such a fluidized-bed process is described, for example, in U.S. Pat. No. 4,409,416 A. In an alternative embodiment, the pyrolysis zone comprises at least one fixed bed. The fixed beds can comprise at least one inert fixed bed of material and/or at least one catalytically active fixed bed of material. If the process of the invention is operated using at least one fixed bed as pyrolysis zone, intermittent operation in which a pyrolysis phase is followed by a burning-off phase in order to remove relatively nonvolatile components from the fixed bed may be advantageous.

To carry out the pyrolysis, a fluidizing gas can be fed into the pyrolysis zone. Preferred fluidizing gases are steam, carbon dioxide, nitrogen, etc., or mixtures of these gases.

In a first preferred embodiment, the pyrolysis is not carried out with addition of hydrogen. In this embodiment, the hydrogenating reaction occurs essentially in the dealkylation step d), if this is present.

In a second preferred embodiment, the pyrolysis is carried out with addition of hydrogen. This embodiment of the pyrolysis can also be referred to as hydrocracking. In hydrocracking, the biomass starting material, especially lignin, is cleaved into low molecular weight fragments by action of hydrogen. The pyrolysis with addition of hydrogen is preferably carried out in suspension. It is also preferably carried out using a catalyst and/or under superatmospheric pressure. Such a process is described, for example, in U.S. Pat. No. 4,420,644 and in H. L. Churn et al., Adv. Solar Energy, Vol. 4 (1988), 91 ff.

In a further preferred embodiment, a black liquor from the Kraft process which has been concentrated by evaporation is used for the pyrolysis. Such a process is, for example, described in U.S. Pat. No. 3,375,283. The black liquor is in this case present predominantly in solid form. In this process variant, too, a pyrolysis gas stream is obtained as product. The solid residue which is likewise obtained can, for example, be recirculated to the pulping process.

In a specific embodiment, a black liquor material which under standard conditions (20° C., 1013 mbar) has a liquid content of not more than 70% by weight, particularly preferably not more than 50% by weight, based on the total weight of the black liquor material, is used for the pyrolysis.

The pyrolysis in step b) can, if desired, be carried out in the presence of at least one pyrolysis catalyst. Suitable pyrolysis catalysts are, for example, silica, alumina, aluminosilicates, aluminosilicates having sheet structures and zeolites such as mordenite, faujasite, zeolite X, zeolite Y and ZSM-5, zirconium oxide or titanium dioxide.

The temperature in the pyrolysis is preferably in the range from 200 to 1500° C., particularly preferably from 250 to 1000° C., in particular from 300 to 800° C.

The pressure in the pyrolysis is preferably in the range from 0.5 to 250 bar (absolute), more preferably from 1.0 to 40 bar (absolute).

The residence time at the pyrolysis temperature can be from a few seconds to a number of days. In a specific embodiment, the residence time at the pyrolysis temperature is from 0.5 second to 5 minutes, especially from 2 seconds to 3 minutes. The residence time, especially in the case of a fluidized-bed reactor, is given by the ratio of the total volume of the reactor to the volume flow of the fluidizing gas under the pyrolysis conditions.

Suitable processes for the catalyzed or uncatalyzed pyrolysis of lignin are, for example, also described in WO 96/09350 (Midwest Research Institute, 1996) or U.S. Pat. No. 4,409,416 (Hydrocarbon Research Institute, 1983), which are hereby incorporated by reference.

In the pyrolysis zone, the biomass starting material, especially the lignin, is converted into a pyrolysis product which under the conditions of the pyrolysis is at least partly gaseous ("pyrolysis gas"). Furthermore, the pyrolysis can result in a pyrolysis product which is partly present as liquid and/or solid under the conditions of the pyrolysis.

The composition of the decomposition product obtained in step b) (=pyrolysis product) can vary as a function of the biomass used.

In any case, the decomposition product obtained in the pyrolysis in step b) comprises oxyaromatics in the sense of the invention. The decomposition product can comprise, in addition to oxyaromatics, further different aromatics and also further components selected from among water vapor, inert gas (e.g. nitrogen), nonaromatic hydrocarbons, $H_2$, CO, $CO_2$, sulfur-comprising compounds such as $H_2S$, etc., and mixtures thereof. The nonaromatic hydrocarbons are preferably degradation products such as methane.

The fractionation and further treatment of the decomposition product obtained in the pyrolysis in step b) will be described in more detail in step c).

$2^{nd}$ Variant: Decomposition in the Liquid Phase

In a second variant of the process of the invention, the biomass starting material, especially the lignin-comprising starting material, is subjected to decomposition in the presence of a liquid decomposition medium in step b). In this variant, the decomposition product is obtained at least partly in the liquid phase.

The decomposition in the liquid phase can be carried out by many processes which differ first and foremost in respect of the decomposition medium. The biomass starting material, especially the lignin-comprising starting material, is preferably subjected to decomposition in the presence of an aqueous-alkaline, aqueous-acidic or organic decomposition medium in step b).

For decomposition in the presence of a liquid decomposition medium in step b), preference is given to using at least one cellulose-depleted fraction from a pulp process. In a specific embodiment, this is a cellulose-depleted fraction from a pulp process which still comprises at least part of the liquid treatment medium from the digestion of the lignocellulose material for pulp production.

The treatment medium used for the decomposition in step b) comprises at least one compound which is liquid under standard conditions (20° C. and 1013 mbar). This is preferably selected from among water, acids, bases, organic solvents and mixtures thereof. In the case of acids and bases which are liquid under standard conditions or liquid mixtures comprising acids or bases, a person skilled in the art can select from those mentioned below. The organic solvents are preferably selected from among alcohols such as methanol, ethanol, n-propanol, isopropanol, n-butanol, tert-butanol or phenol, diols and polyols such as ethanediol and propanediol, amino alcohols such as ethanolamine, diethanolamine or triethanolamine, aromatic hydrocarbons such as benzene, toluene, ethylbenzene or xylenes, halogenated solvents such as dichloromethane, chloroform, carbon tetrachloride, dichloroethane or chlorobenzene, aliphatic solvents such as pentane, hexane, heptane, octane, ligroin, petroleum ether, cyclohexane or decalin, ethers such as tetrahydrofuran, diethyl ether, methyl tert-butyl ether or diethylene glycol monomethyl ether, ketones such as acetone or methyl ethyl ketone, esters such as ethyl acetate, formamide, dimethylformamide (DMF), dimethylacetamide, dimethyl sulfoxide (DMSO), acetonitrile and mixtures thereof.

The liquid compound is preferably selected from among water, water-miscible organic solvents and mixtures thereof.

The liquid compound is particularly preferably selected from among water, alcohols and mixtures thereof. It is thus possible to use water, methanol, ethanol, a mixture of water with methanol and/or ethanol or a mixture of methanol and ethanol as liquid compound.

The liquid decomposition medium used in step b) can comprise at least one base. Suitable bases are alkali metal and alkaline earth metal hydroxides, e.g. sodium hydroxide, potassium hydroxide, calcium hydroxide or magnesium hydroxide, alkali metal and alkaline earth metal hydrogencarbonates, e.g. sodium hydrogencarbonate, potassium hydrogencarbonate, calcium hydrogencarbonate or magnesium hydrogencarbonate, alkali metal and alkaline earth metal carbonates, e.g. sodium carbonate, potassium carbonate, calcium carbonate or magnesium carbonate, alkaline earth metal oxides such as calcium oxide or magnesium oxide and mixtures thereof.

The liquid decomposition medium used in step b) can comprise at least one acid. Brönsted acids or Lewis acids are suitable in principle. Suitable Brönsted acids are inorganic acids and their acidic salts and anhydrides. These include, for example, mineral acids such as hydrochloric acid, nitric acid, sulfuric acid, phosphoric acid or amidosulfonic acid, but also ammonium salts such as ammonium fluoride, ammonium chloride, ammonium bromide or ammonium sulfate. Hydrogensulfates such as sodium hydrogensulfate, potassium hydrogensulfate, calcium hydrogensulfate or magnesium hydrogensulfate are also suitable. Hydrogen sulfites such as sodium hydrogensulfite, potassium hydrogensulfite, calcium hydrogensulfite or magnesium hydrogensulfite are also suitable. Hydrogenphosphates and dihydrogenphosphates such as sodium hydrogenphosphate, sodium dihydrogenphosphate, potassium hydrogenphosphate or potassium dihydrogenphosphate are also suitable. $SO_2$, $SO_3$ and $CO_2$ are also suitable.

Further suitable Brönsted acids are organic acids and anhydrides thereof, e.g. formic acid, acetic acid, methanesulfonic acid, trifluoroacetic acid or p-toluenesulfonic acid. Suitable Lewis acids are all metal or semimetal halides in which the metal or semimetal has an electron pair gap. Examples are $BF_3$, $BCl_3$, $BBr_3$, $AlF_3$, $AlCl_3$, $AlBr_3$, ethylaluminum dichloride, diethylaluminum chloride, $TiF_4$, $TiCl_4$, $TiBr_4$, $VCl_5$, $FeF_3$, $FeCl_3$, $FeBr_3$, $ZnF_2$, $ZnCl_2$, $ZnBr_2$, $Cu(I)F$, $Cu(I)Cl$, $Cu(I)Br$, $Cu(II)F_2$, $Cu(II)Cl_2$, $Cu(II)Br_2$, $Sb(III)F_3$, $Sb(V)F_5$, $Sb(III)Cl_3$, $Sb(V)Cl_5$, $Nb(V)Cl_5$, $Sn(II)F_2$, $Sn(II)Cl_2$, $Sn(II)Br_2$, $Sn(IV)F_4$, $Sn(IV)Cl_4$ and $Sn(IV)Br_4$.

The liquid decomposition medium used in step b) can comprise at least one salt other than the compounds mentioned above. These salts are preferably selected from among salts of the abovementioned acids and bases and also oxidation or reduction products thereof. Suitable salts are, for example, ammonium, alkali metal or alkaline earth metal sulfates such as sodium sulfate, potassium sulfate, calcium sulfate or magnesium sulfate. Ammonium, alkali metal or alkaline earth metal sulfites such as sodium sulfite, potassium sulfite, calcium sulfite or magnesium sulfite are also suitable. Ammonium, alkali metal or alkaline earth metal sulfides such as sodium sulfide, potassium sulfide, calcium sulfide or magnesium sulfide are also suitable. Alkali metal hydrogensulfides such as sodium hydrogensulfide or potassium hydrogensulfide are also suitable.

The liquid decomposition medium used in step b) can comprise further compounds other than the abovementioned compounds. These are especially the customary process chemicals known to a person skilled in the art from the various digestion processes for producing pulp from a lignocellulose-comprising starting material. Such processes and the process chemicals used therein are known to those skilled in the art.

In a first particularly preferred embodiment, an alkaline decomposition medium is used in step b). In particular, at least one cellulose-depleted fraction from a pulp process which comprises at least part of the alkaline digestion medium from the preceding pulp process is used for the decomposition in step b).

The decomposition in step b) is then preferably carried out using a cellulose-depleted fraction from the Kraft process (sulfate process). The decomposition medium used in step b) then comprises NaOH and $Na_2S$ in an aqueous medium. In a specific embodiment, the treatment medium used in step a) comprises NaOH, $Na_2S$, $Na_2CO_3$ and $Na_2SO_4$ in an aqueous medium.

The decomposition in step b) is particularly preferably carried out using a black liquor obtained in the production of pulp by the Kraft process. Here, it is possible to use either the black liquor obtained directly after the pulp fibers have been separated off ("weak black liquor") or a concentrated grade obtained by evaporation. Decomposition in an alkaline aqueous phase as described by Clark and Green in Tappi, 51(1), 1968, 44 ff, is particularly advantageous.

The decomposition in step b) can also be carried out using a cellulose-depleted fraction from the soda process (sodium carbonate process). The treatment medium used in step b) then comprises NaOH as main component in an aqueous medium which is essentially free of sulfur-comprising compounds.

The decomposition in step b) can also be carried out using a cellulose-depleted fraction from the alkali-oxygen digestion.

The decomposition in step b) can also be carried out using a cellulose-depleted fraction from the alkali-peroxide digestion.

The decomposition in step b) can also be carried out using a cellulose-depleted fraction from digestion in the presence of anthraquinone.

The decomposition in step b) can also be carried out using a cellulose-depleted fraction from the digestion of lignocellulose material by means of organic solvents (also referred to as Organosolv process). Suitable organic solvents are those mentioned above. In particular, an organic solvent selected from among $C_1$-$C_4$-alkanols, mixtures of $C_1$-$C_4$-alkanols and mixtures of at least one $C_1$-$C_4$-alkanol with water is used. The $C_1$-$C_4$-alkanols are preferably selected from among methanol, ethanol, n-propanol, isopropanol and n-butanol. Preference is given to methanol, ethanol and mixtures thereof. Mixtures of at least one $C_1$-$C_4$-alkanol with water preferably comprise from 10 to 99% by weight, particularly preferably from 20 to 95% by weight, of at least one $C_1$-$C_4$-alkanol, based on the total weight of the mixture. The decomposition medium used in step b) can then additionally comprise an additive from the parent pulp process. Such additives include, for example, alkali metal hydroxides such as sodium hydroxide; ammonium hydrogensulfite and also alkali metal and alkaline earth metal hydrogensulfites such as sodium hydrogensulfite and magnesium hydrogensulfite. They also include mineral acids such as hydrochloric acid, nitric acid, sulfuric acid, phosphoric acid or amidosulfonic acid and the ammonium, alkali metal and alkaline earth metal salts thereof. Organic acids such as oxalic acid, formic acid or acetic acid are also suitable as acids. Peracids such as persulfuric acid or peracetic acid are also suitable.

The cellulose-depleted fractions which comprise at least part of the liquid treatment medium from one of the following commercial Organosolv processes:
Alcell process: Ethanol/water mixture as treatment medium;
ASAM process: Alkaline sulfite-anthraquinone-methanol treatment medium;
Organocell process: Two-stage process using an organic medium in the first stage and an alkali medium in the second stage, e.g. digestion by means of methanol and/or ethanol in the first stage and by means of methanol and/or ethanol, NaOH and optionally anthraquinone in the second stage;
Acetosolv process: Acetic acid/hydrochloric acid mixture as treatment medium;
are also suitable for use in step b) of the process of the invention.

The decomposition in the presence of a liquid decomposition medium in step b) can be carried out in one or more stages. In the simplest case, the decomposition in step b) is carried out in one stage.

The decomposition in step b) is preferably carried out at above ambient temperature. The temperature is preferably in the range from about 40 to 300° C., particularly preferably from 50 to 250° C. In a specific embodiment, the temperature is firstly increased stepwise or continuously during the course of the treatment until the desired final temperature has been reached.

The decomposition in step b) can be carried out under reduced pressure, at ambient pressure or at above ambient pressure. The pressure in step a) is generally in the range from 0.01 bar to 300 bar, preferably from 0.1 bar to 100 bar.

The duration of the decomposition in step b) is generally from 0.5 minute to 7 days, preferably from 5 minutes to 96 hours.

If a cellulose-depleted fraction from the pulp process is used for the decomposition in step b), the decomposition is advantageously carried out in the proximity of the site of pulp production in order to keep the transport costs for the cellulose-depleted fraction, especially a black liquor, low. Transport is preferably effected via a pipeline.

In any case, the decomposition product obtained in the decomposition in the presence of a liquid decomposition medium in step b) comprises oxyaromatics in the sense of the invention.

The fractionation and further treatment of the decomposition product obtained in the presence of a liquid decomposition medium in step b) is described in more detail in step c).

It is in principle possible to use the decomposition product obtained in step b) without further fractionation and/or treatment for the dealkylation in step d) or for the amination in step e). If the decomposition product obtained in step b) is obtained as a liquid, this is preferably subjected to evaporation before introduction into step d) or into step e). A preferred embodiment of evaporation is depicted in FIG. 1 and described below.

In another embodiment of the process of the invention, the decomposition product obtained in step b) is subjected to a fractionation and/or treatment (step c) before use in the dealkylation (step d) or the amination (step e).

Fractionation/Treatment of the Decomposition Product (Step c)

The decomposed material obtained in step b) is preferably separated in step c) into at least one aromatics-enriched fraction C1) and at least one aromatics-depleted fraction C2).

The fractionation is preferably carried out by distillation, extraction, absorption, membrane processes or a combination thereof. The fractionation is particularly preferably carried out by distillation, extraction or a combination thereof.

If the decomposition in step b) is carried out in the liquid phase, the fractionation in step c) is preferably carried out by means of distillation and/or extraction.

In a first specific embodiment of the process of the invention, the biomass starting material provided in step a) is subjected to decomposition in the liquid phase in step b) and the fractionation in step c) to give at least one aromatics-enriched fraction C1) and at least one aromatics-depleted fraction C2) preferably comprises an extraction and/or a distillation.

Before the fractionation in step c), the pH of the discharge from a decomposition in the liquid phase in step b) is preferably set to a desired value. In a specific embodiment, a decomposition product which has been obtained by decomposition in the presence of an alkaline decomposition medium is used in step c). In particular, at least one cellulose-depleted fraction from a pulp process, in particular a black liquor from the Kraft process, is used for the decomposition. The pH is then preferably set to a value of not more than 9, particularly preferably not more than 8, by addition of acid before fractionation of the decomposition product. Suitable acids are, for example, mineral acids such as hydrochloric acid, sulfuric acid and phosphoric acid and also acid-forming compounds such as $CO_2$ and $H_2S$. Preference is given to using $CO_2$ from an offgas stream of the process of the invention or of a pulp process coupled with the process of the invention. For example, the offgas from a black liquor combustion (recovery boiler) or a lime kiln is suitable. Here, the offgas can be introduced into the decomposition product either directly or after removal of the other components (e.g. by means of a scrubbing process such as a Benfield scrub). The carbonates and/or hydrogencarbonates formed by addition of $CO_2$ can generally be recirculated in a simple manner, e.g. to a pulp process coupled with the decomposition process, e.g. to a black liquor which has been taken off beforehand for lignin recovery. The use of $CO_2$ for adjusting the pH is thus associated with lower costs than the use of other acids and in addition generally makes good integration into a pulp process possible. The hydroxyaromatics obtained in the decomposition in step b) are virtually completely present as salts (phenoxides) at pH values above about 9. Prior reduction of the pH to a value of <9, preferably <8, aids effective isolation by distillation and/or extraction.

The fractional distillation of the product obtained in step b) from decomposition in the liquid phase can be carried out by customary processes known to those skilled in the art. Preference is given to steam distillation, in which an aromatics-enriched distillate is obtained. This mode of operation utilizes the steam volatility of the aromatic fragments obtained in the decomposition in step b) in order to separate them off from the decomposition product. Preference is given to a multistage process in which the heat of condensation of the vapor in at least one stage is utilized for the vaporization in another stage. The distillation product obtained is enriched in aromatics compared to the decomposition product used and is suitable, optionally after removal of the aqueous phase, as starting material for the optional dealkylation in step d) or the amination in step e).

The fractionation of the product obtained in step b) from the decomposition in the liquid phase is also preferably carried out by extraction. Here, at least part of the aromatics obtained in the decomposition in step b) is separated off, while the remaining residue (organic components which are low in aromatics, inorganic process chemicals, etc.) can be passed to a further work-up and/or thermal utilization, preferably in the process of the invention or an integrated process for pulp production coupled therewith.

The extraction can be carried out using a solvent (extractant) in which the aromatics obtained in the decomposition are soluble in a sufficient amount and which otherwise forms a miscibility gap with the decomposition product. The extractant is then brought into intimate contact with the decomposition product obtained in step b) and a phase separation is subsequently carried out. The extraction can have one or more stages.

Suitable extractants are organic compounds such as aromatic or nonaromatic hydrocarbons, alcohols, aldehydes, ketones, amides, amines and mixtures thereof. These include, for example, benzene, toluene, ethylbenzene, xylenes, pentane, hexane, heptane, octane, ligroin, petroleum ether, cyclohexane, decalin, n-butanol, sec-butanol, tert-butanol, 1-pentanol, 1-hexanol, 1-heptanol, 1-octanol, methyl ethyl ketone and mixtures thereof.

The extraction can be carried out batchwise or continuously, see description in: K. Sattler, Thermische Trennverfahren, Wiley-VCH, third substantially revised and expanded edition, July 2001. A plurality of batch separation operations can be carried out successively in the manner of a cascade, with the residue separated off from the extractant phase in each case being brought into contact with a fresh proportion of extractant and/or the extractant being conveyed in countercurrent. To carry out the extraction batchwise, the decomposition product and the extractant are brought into contact with mechanical agitation, e.g. by means of stirring, in a suitable vessel, the mixture is allowed to stand to enable phase separation to occur and one of the phases is removed, advantageously by taking off the heavier phase at the bottom of the vessel. To carry out the extraction continuously, the extractant and the decomposition product are conveyed continuously in a suitable apparatus in a manner analogous to the batch variant.

The extraction is carried out, for example, in at least one mixer-settler combination or at least one extraction column. Suitable mixers include both dynamic and static mixers.

In a preferred embodiment, the fractionation to give at least one aromatic-enriched fraction C1) and at least one aromatics-depleted fraction C2) in step c) comprises the following substeps:

c1) Extraction of the decomposition product obtained in step b) to give an aromatics-enriched extract and an aromatics-depleted residue,
c2) optionally separation of the extract into a fraction enriched in extractant and depleted in aromatics and a fraction enriched in aromatics and depleted in extractant,
c3) introduction of the aromatics-enriched extract obtained in step c1) or the aromatics-enriched fraction obtained in step c2) into step d) and/or e).

Before the extraction, the pH of the decomposition product obtained in step b) can be adjusted by addition of at least one acid or at least one base. Furthermore, in the case of a multistage extraction, the pH of the decomposition product introduced into the first stage and the pH of the residue separated off from the extractant phase in the respective stage can be adjusted by addition of at least one acid or acid-forming compound or at least one base. Suitable acids are, for example, mineral acids such as hydrochloric acid, sulfuric acid and phosphoric acid, or acid-forming compounds such as $CO_2$ and $H_2S$. Suitable bases are, for example, alkali metal bases such as sodium hydroxide or potassium hydroxide, alkali metal carbonates such as sodium carbonate or potassium carbonate, alkali metal hydrogencarbonates such as sodium hydrogencarbonate or potassium hydrogencarbonate and alkaline earth metal bases such as calcium hydroxide, calcium oxide, magnesium hydroxide or magnesium carbonate and also ammonia or amines.

The separation of the extract in step c2) into an extractant-enriched fraction and an aromatics-enriched fraction C1) is preferably carried out by distillation.

The fractional distillation of the extract in step c2) can be carried out by conventional processes known to those skilled in the art. Suitable processes are described in: K. Sattler, Thermische Trennverfahren, Wiley-VCH, third substantially revised and expanded edition, July 2001. Suitable apparatuses for the fractional distillation comprise distillation columns such as tray columns which may be provided with bubble caps, sieve plates, sieve trays, ordered packing, internals, valves, side offtakes, etc. Dividing wall columns which may be provided with side offtakes, recirculations, etc., are especially suitable. A combination of two or more than two distillation columns can be used for the distillation. Evaporators such as thin film evaporators, falling film evaporators, Sambay evaporators, etc., and combinations thereof are also suitable.

If the decomposition in step b) comprises a pyrolysis, the fractionation in step c) is preferably carried out by means of absorption.

In a second embodiment of the process of the invention, the biomass starting material provided in step a) is subjected to a pyrolysis to effect decomposition in step b) and the fraction in step c) to give at least one aromatics-enriched fraction C1) and at least one aromatics-depleted fraction C2) comprises an absorption.

The discharge taken from the pyrolysis zone can comprise not only the pyrolysis gases but also amounts of solid and/or liquid components. These are, for example, relatively nonvolatile components (e.g. carbonaceous material) formed in the pyrolysis. If at least one solid additional material is used for the pyrolysis in step b), the discharge from the pyrolysis zone can also comprise amounts of the additional material. These solid and/or liquid components can, if desired, be separated off from the pyrolysis gas in step c) by means of a suitable apparatus, e.g. a cyclone. Solid additional materials which have been separated off are preferably recirculated to the pyrolysis zone. Components other than additional materials which have been separated off are passed to another use, e.g. combustion to generate heat which is preferably reused in the process of the invention or an integrated process. The offgas obtained here, which comprises predominantly $CO_2$ and also water and optionally $O_2$, can likewise be passed to a use. It is also possible to bring a discharge from the pyrolysis zone comprising at least one additional material and components which are relatively nonvolatile under the pyrolysis conditions into contact with an oxygen-comprising gas, preferably air, in a burning-off zone physically separate from the pyrolysis zone, which leads to burning-off of relatively nonvolatile components formed in the pyrolysis ("carbonaceous material"). The additional material is then separated off from the resulting offgas by means of a suitable separation device and returned via a suitable transport device to the pyrolysis zone.

In a suitable embodiment, the discharge from the pyrolysis can be fed directly, i.e. without removal of condensable components, into an optional subsequent dealkylation zone. However, components of the discharge from the pyrolysis zone which are relatively nonvolatile under the conditions of the pyrolysis in step b) and are not present in gaseous form but rather in solid or liquid form in the discharge from the pyrolysis zone can be separated off before introduction into the dealkylation zone in this embodiment. In a particular embodiment, on the other hand, condensable pyrolysis products (i.e. products which are present as liquids or solids under normal conditions) are separated off from the discharge from the pyrolysis (after removal of solid/liquid). This can be effected by means of suitable separation processes known to those skilled in the art, e.g. condensation, absorption, adsorption, membrane separation processes, etc.

A particularly preferred variant is absorption. Here, the discharge from the pyrolysis zone is brought into contact with a stream Ab1) which comprises a suitable solvent. Contacting is preferably carried out after a cooling step in which condensation of high-boiling components can also take place. Contacting is carried out in a suitable apparatus (e.g. a column). A liquid stream Ab2) which comprises the absorption medium and aromatic pyrolysis products and a gaseous stream Ab3) which is enriched in aromatic pyrolysis products compared to the discharge from the pyrolysis flow out from the contact apparatus. Stream Ab2) is separated, preferably by distillation, into a fraction Ab4) which is enriched in aromatic pyrolysis products compared to Ab2) and a fraction Ab5) which is depleted in aromatic pyrolysis products compared to Ab2). Ab4) is, if necessary after further work-up, fed as stream C1) to the optional subsequent dealkylation step d) or the amination step e) and Ab5) is, after further cooling, recirculated to the absorption, i.e. Ab5 is the main constituent of Ab1). A further constituent is a proportion of solvent which is added to compensate solvent losses.

Solvents suitable as absorption media are organic compounds such as aromatic or nonaromatic hydrocarbons, alcohols, aldehydes, ketones, amides, amines and mixtures thereof. These include, for example, benzene, toluene, ethylbenzene, xylenes, pentane, hexane, heptane, octane, ligroin, petroleum ether, cyclohexane, decalin, methanol, ethanol, n-propanol, isopropanol, n-butanol, sec-butanol, tert-butanol, 1-pentanol, 1-hexanol, 1-heptanol, 1-octanol, acetaldehyde, acetone, methyl ethyl ketone, N-methylpyrrolidone, dimethylformamide, dimethylacetamide and mixtures thereof.

The solvent preferably has a boiling point which under identical conditions is below that of phenol. The solvent particularly preferably has a boiling point which under identical conditions is at least 10 K below that of phenol. The solvent preferably additionally has a high solubility in water. Such solvents include, for example, methanol, ethanol, n-propanol, isopropanol, n-butanol, sec-butanol and tert-butanol.

Many of the solvents used as absorption media have a vapor pressure under the conditions of the absorption and this leads to loading of the gas stream Ab3) leaving the absorption with the absorption medium. This applies especially to the preferred solvents having a boiling point below the boiling point of phenol. The gas stream Ab3) leaving the absorption is then preferably subjected to an at least partial removal of the solvent comprised. The removal of the solvent from the gas stream Ab3) is preferably carried out in the form of a water scrub. Here, good water solubility of the solvent used for absorption is particularly advantageous. The scrubbing water stream loaded with solvent and optionally aromatics can, for example, be worked up by distillation. The absorption medium separated off is (optionally together with the aromatics) recirculated to the absorption step.

The decomposition product obtained in step b) can be subjected in step c) not only to the abovementioned fractionation but also to at least one further treatment step. Additional treatment steps can be carried out before, during or after the fractionation.

The decomposition product obtained in step b) or the fraction C1) isolated therefrom in step c) comprises predominantly components having a molecular weight of not more than 500 g/mol, particularly preferably not more than 400 g/mol, in particular not more than 300 g/mol.

In a specific embodiment of the process of the invention, the aromatics-depleted fraction C2) isolated in step c) is used at least partly for the production of synthesis gas.

Dealkylation (Step d)

The decomposition product from step b) or the aromatics-enriched fraction C1) from step c) is optionally fed into a dealkylation zone and reacted in the presence of hydrogen and/or water vapor. In the dealkylation, the aromatic degradation products which have been formed in the pyrolysis in step b) and optionally isolated as fraction C1) in step c) can be at least partly transformed by action of hydrogen and/or water vapor so as to replace substituents by hydrogen and/or cleave compounds comprising a plurality of aromatic rings to form compounds having a lower number of rings. As indicated above, "dealkylation" thus also refers to reactions in which no alkyl substituent is replaced by hydrogen, e.g. dehydroxylation, dealkoxylation, aromatics cleavage, etc. The substituents replaced by hydrogen are preferably selected from among alkyl groups.

Dealkylation processes suitable for use in step d) comprise hydrodealkylation, steam dealkylation or mixed forms thereof. In the case of a pure hydrodealkylation for the purposes of the invention, molecular hydrogen (in pure form or in admixture with other components such as CO) but no water is fed in addition to the pyrolysis gas stream into the dealkylation zone. In the case of a pure steam dealkylation for the purposes of the invention, water (in pure form or in admixture with other components) but no molecular hydrogen is fed in addition to the pyrolysis gas stream into the dealkylation zone. The dealkylation process in step d) can also be configured as a mixed form of hydrodealkylation and steam dealkylation. In this case, both water and molecular hydrogen are fed in addition to the pyrolysis gas stream into the dealkylation zone. Suitable and preferred process parameters are, in part, indicated below for hydrodealkylation and steam dealkylation. This information enables a person skilled in the art to determine suitable and preferred process parameters for a mixed form of hydrodealkylation and steam dealkylation. The reaction gas composed of $H_2$ and $H_2O$ used for the dealkylation then preferably has a mixing ratio of $H_2$ to $H_2O$ in the range from about 0.1:99.9 to 99.9:0.1. An especially suitable mixing ratio of $H_2$ to $H_2O$ is in the range from about 40:60 to 60:40.

The hydrogen required for the reaction is in the case of steam dealkylation formed in situ by reaction of water with (mainly organic) components which are either comprised in the feed mixture to the steam dealkylation or are formed during the course of the steam dealkylation. The formation of hydrogen from methane and water according to the equation $CH_4+H_2O \rightarrow CO+3H_2$ may be mentioned by way of example here.

The temperature in the dealkylation zone is preferably in the range from 400 to 900° C., particularly preferably from 500 to 800° C.

The absolute pressure in the dealkylation zone is preferably in the range from 1 to 100 bar, particularly preferably from 1 to 20 bar.

In a first preferred embodiment, the decomposition product from step b) or the aromatics-enriched fraction C1) is subjected to a hydrodealkylation. For this purpose, the reaction in step d) is carried out in the presence of hydrogen.

The temperature in the dealkylation zone for the hydrodealkylation is preferably in the range from 500 to 900° C., particularly preferably from 600 to 800° C.

The absolute pressure in the dealkylation zone for the hydrodealkylation is preferably in the range from 1 to 100 bar, particularly preferably from 1 to 20 bar, in particular from 1 to 10 bar.

The ratio of $H_2$ used to $H_2$ (stoichiometric) in the hydrodealkylation is preferably in the range from 0.02 to 50, particularly preferably from 0.2 to 10. Here, $H_2$ (stoichiometric) is the amount of $H_2$ which is theoretically required for complete conversion of the aromatics fed into the dealkylation zone into benzene, under the assumption that 1 mol of $H_2$ reacts per ring substituent.

The residence time in the dealkylation zone for the hydrodealkylation is preferably in the range from 0.1 to 500 s, particularly preferably from 0.5 to 200 s.

In a second preferred embodiment, the decomposition product from step b) or the aromatics-enriched fraction C1) from step c) is subjected to a steam dealkylation. For this purpose, the reaction in step d) is carried out in the presence of water vapor.

The temperature in the dealkylation zone for the steam dealkylation is preferably in the range from 400 to 800° C., particularly preferably from 475 to 600° C., in particular from 525 to 600° C.

The absolute pressure in the dealkylation zone for the steam dealkylation is preferably in the range from 1 to 100 bar, particularly preferably from 1 to 20 bar, in particular from 1 to 10 bar.

The ratio of $H_2O$ used to C* in the steam dealkylation is preferably in the range from 0.1 to 20 mol/mol, particularly preferably from 0.5 to 2 mol/mol. Here, C* is the molar amount of carbon, determined by carbon-based balancing of the pyrolysis or by determination of the amounts of products discharged from the steam dealkylation by means of methods known to those skilled in the art.

The molar ratio of $H_2$ to $CH_4$ in the dealkylation zone in the steam dealkylation is preferably in the range <50:1, particularly preferably <25:1.

In the case of a steam dealkylation in the absence of a dealkylation catalyst, the molar ratio of OR (where R=H, alkyl) to $C_{total}$ in the dealkylation zone is preferably in the range >0.05:1, particularly preferably from 0.1:1 to 0.2:1.

In the case of a steam dealkylation in the absence of a dealkylation catalyst, the ratio of OR (where R=H, alkyl) to $C_{eliminatable}$ in the dealkylation zone is preferably in the range >0.5:1, particularly preferably from 1:1 to 10:1, in particular from 1:1 to 2:1.

The WHSV for the steam dealkylation is preferably in the range from 0.05 to 10 kg/L*h, particularly preferably from 0.1 to 2 kg/L*h.

The steam dealkylation can be carried out in the presence or absence of a catalyst. In a specific embodiment, the steam dealkylation is carried out in the absence of a catalyst. A catalyzed process for steam dealkylation is described in WO 2008/148807 A1. This document and the references cited therein in respect of suitable catalysts are hereby fully incorporated by reference. Further information on types of catalyst and process steps in the steam dealkylation may be found in WO 2007/051852 A1, WO 2007/051851 A1, WO 2007/051855 A2, WO 2007/051856 A1, WO 2008/135581 A1 and WO 2008/135582 A1 (EP 2008055585), without this constituting a restriction. U.S. Pat. No. 3,775,504 states that a steam dealkylation actually comprises a combination of steam dealkylation and hydrodealkylation, since it is inherent in the system that at least part of the hydrogen produced is immediately reacted again.

The dealkylation step d) gives at least one oxyaromatics composition which generally has smaller proportions of the following components than the decomposition product from step b) or the aromatics-enriched fraction C1) from step c): monoalkylated, dialkylated and polyalkylated phenols; alkoxyphenols such as methoxyphenols; polyalkylated benzenes; compounds comprising two or more aromatic rings. These components will hereinafter be referred to as "aromatics which have not been dealkylated or been dealkylated to only a small extent".

Fractionation of the discharge from the dealkylation zone

The discharge from the dealkylation zone can be fed directly to the amination in step e).

In an alternative embodiment, a discharge is taken from the dealkylation zone and subjected to fractionation before introduction into the amination in step e). Here, at least one stream D1) enriched in dealkylated oxyaromatics and at least one stream D2) enriched in volatile components are obtained. An oxyaromatics composition having a high content of monocyclic oxyaromatics which are unalkylated or have a low degree of alkylation is preferably obtained as product D1).

The discharge from the dealkylation zone is preferably subjected to fractionation to give the following three streams:
D1) a stream enriched in monocyclic oxyaromatics which are unalkylated or have a low degree of alkylation,
D2) a stream enriched in aromatics which have not been dealkylated or been dealkylated to only a small extent,
D3) a stream enriched in by-products which are more volatile than D1) and D2).

The discharge from the dealkylation zone can optionally be subjected to fractionation to give further streams such as a water-comprising stream.

The stream D1) is advantageous for use in the amination step e).

The stream D1) preferably comprises at least 70% by weight, particularly preferably at least 80% by weight, in particular at least 90% by weight, based on the total amount of D1), of monocyclic aromatics.

The stream D1) preferably comprises not more than 30% by weight, particularly preferably not more than 20% by weight, in particular not more than 10% by weight, based on the total amount of D1), of aromatics which have not been dealkylated or been dealkylated to only a small extent.

The stream D2) preferably comprises at least 70% by weight, particularly preferably at least 80% by weight, in particular at least 90% by weight, based on the total amount of D2), of aromatics which have not been dealkylated or been dealkylated to only a small extent.

The stream D3) comprises components which are selected, for example, from among nonaromatic hydrocarbons, especially methane, hydrogen, carbon monoxide, carbon dioxide and mixtures thereof. Depending on the lignin-comprising starting material provided in step a), the stream D3) can comprise further components. When a lignin-comprising starting material from the Kraft process is used, these include sulfur-comprising by-products, especially $H_2S$.

Preference is given to taking a gaseous discharge from the dealkylation zone and subsequently subjecting it to fractionation.

As fractionation processes, it is possible to use the generally known thermal separation processes.

The fractionation of the discharge from the dealkylation zone in step d) preferably comprises an absorption. In the absorption, the gaseous discharge from the dealkylation zone is brought into contact with a solvent (absorption medium), with part of the components comprised in the gas stream being absorbed and thus separated off.

The absorption is carried out in a suitable apparatus, e.g. a countercurrent column, bubble column, etc. The absorption is preferably carried out in a countercurrent column.

The absorption can have one or more stages.

The absorption is preferably carried out using a solvent (unloaded: absorbent, loaded: absorbate) in which the aromatics obtained in the dealkylation are soluble in a sufficient amount and the other volatile by-products are essentially insoluble. Here, the aromatics which have not been dealkylated or been dealkylated to only a small extent are also absorbed together with the monocyclic aromatics which are unalkylated or have a low degree of alkylation (=target product).

The absorption thus gives, firstly, an absorbate loaded with aromatics. The aromatic components comprised in the absorbate correspond in terms of their composition to the sum of the aromatics in the streams D1) and D2) plus aromatics optionally comprised in the absorption medium. The components comprised in the remaining gas stream correspond in terms of their composition to the stream D3). If desired, the gas stream can be subjected to an additional purification step to remove aromatics. These can then be combined again with the aromatics comprised in the solvent which has been separated off for joint work-up. However, such isolation of aromatics from the gas stream which has been separated off is generally not necessary.

In a preferred embodiment, the fractionation of the discharge from the dealkylation zone in step d) comprises the following substeps:
d1) contacting of the discharge from the dealkylation zone with an absorption medium to give an absorbate enriched in aromatic main products of the dealkylation and a gas stream D3) depleted in aromatic main products of the dealkylation,
d2) separation of the absorbate into a stream D1) enriched in monocyclic oxyaromatics which are unalkylated or have a low degree of alkylation, a stream D2) enriched in aromatics which have not been dealkylated or been dealkylated to only a small extent and optionally a stream comprising the absorption medium,
d3) if present, recirculation of the stream comprising the absorption medium to step d1),
d4) optionally recirculation of at least part of the stream D2) to the dealkylation zone of step d).

The absorption medium preferably has a boiling point which is above the boiling point of the highest-boiling component of the stream D1.

In a first suitable embodiment, an absorption medium which is different from the components of streams D1) and D2) is used. Suitable absorption media for this embodiment are nonaromatic hydrocarbons, nonaromatic alcohols, nonaromatic aldehydes, ketones, amides, amines and mixtures thereof. The absorption medium for this embodiment is preferably selected from among pentane, hexane, heptane, octane, ligroin, petroleum ether, cyclohexane, decalin, methanol, ethanol, n-propanol, isopropanol, n-butanol, sec-butanol, tert-butanol, 1-pentanol, 1-hexanol, 1-heptanol, 1-octanol, acetaldehyde, acetone, methyl ethyl ketone, N-methylpyrrolidone, dimethylformamide, dimethylacetamide and mixtures thereof.

Further suitable absorption media are aromatic hydrocarbons different from the components of streams D1) and D2). These aromatic hydrocarbons are preferably selected from among optionally substituted acetophenones, optionally substituted benzophenones, optionally substituted biphenyls, optionally substituted terphenyls, optionally substituted diphenyl ethers and mixtures thereof. If a component which is also comprised as by-product in the streams D1) or D2) is used as absorption medium, it can be ensured by means of instrumentation measures known to those skilled in the art that this component is continuously removed from the process in the amount in which it is obtained.

When an absorption medium which is different from the components of the streams D1) and D2) is used, the fractionation of the discharge from the dealkylation zone in step d) preferably comprises the following substeps:

d1) contacting of the discharge from the dealkylation zone with an absorption medium to give an absorbate enriched in aromatic main products of the dealkylation and a gas stream D3) depleted in aromatic main products of the dealkylation (or a gas stream D3) enriched in by-products which are more volatile than D1 and D2), d2) separation of the absorbate into a stream D1) enriched in monocyclic oxyaromatics which are unalkylated or have a low degree of alkylation, a stream D2) enriched in aromatics which have not been dealkylated or been dealkylated to only a small extent and a stream comprising the absorption medium, d3) recirculation of the stream comprising the absorption medium to step d1), d4) optionally recirculation of at least part of the stream D2) to the dealkylation zone of step d).

In a specific variant, an aromatics composition which can be obtained by the process of the invention is used as absorption medium. This is especially a mixture of aromatics which have not been reacted or been incompletely reacted in the dealkylation. In a preferred variant, an aromatics composition whose composition corresponds partly or completely to the stream D2 or a mixture of D1 and D2 is used as absorption medium. The stream D2 or the mixture of D1 and D2 can optionally be subjected to at least one work-up step before use as absorption medium.

When an absorption medium whose composition corresponds largely or completely to the stream D2 or a mixture of D1 and D2 is used, the fractionation of the discharge from the dealkylation zone in step d) preferably comprises the following substeps:

d1) contacting of the discharge from the dealkylation zone with an absorption medium to give an absorbate enriched in aromatic main products of the dealkylation and a gas stream D3) depleted in aromatic main products of the dealkylation, d2) separation of the absorbate into a stream D1) enriched in monocyclic oxyaromatics which are unalkylated or have a low degree of alkylation and a stream D2) enriched in aromatics which have not been dealkylated or been dealkylated to only a small extent, d4) optionally recirculation of at least part of the stream D2) to the dealkylation zone of step d).

In this variant, the solvent can be obtained by partial condensation of the stream from the dealkylation or of a gas stream from a preliminary removal of high boilers downstream of the dealkylation. Here, it can be advantageous to insert a further partial condensation in which water, in particular, is condensed out between the abovementioned partial condensation and the absorption. In this variant too, at least partial absorption of the unreacted or incompletely reacted aromatics takes place together with the absorption of desired product, that is to say, in this variant too, the aromatic components comprised in the absorbate correspond in terms of their composition to the sum of the aromatics of the streams D1) and D2).

In step d2), the aromatics-enriched absorbate is preferably fractionated by distillation. The solvent recovered is, optionally after removal of absorbed water, recirculated to the absorption (step d1). The aromatics are processed further as described above and in the following.

The aromatics-enriched absorbate is preferably fractionally distilled in at least one column ("regeneration column") in step d2). The distillation conditions are preferably selected so that essentially aromatics which are unalkylated or have a low degree of alkylation and, if present, water are obtained as overhead product and essentially the aromatics which have not been dealkylated or been dealkylated to only a small extent are obtained as bottom product.

It goes without saying that the temperature at the bottom selected in the fractional distillation in step d2) is so low that undesirable secondary reactions of the bottom product are essentially avoided. This can be achieved, in particular, by selling a suitable column pressure and/or the low boiler content in the bottoms (the low boiler content can be reduced further by means of subsequent stripping).

The overhead product obtained in the distillation in step d2) can be taken off directly as stream d1) and used for the amination in step e).

As an alternative, the overhead product obtained in the distillation in step d2) can be subjected to a further work-up.

Water comprised in the overhead product can be separated off by known methods. For this purpose, the overhead product can, after condensation of the vapor from the distillation, be fed to a phase separator in order to separate off water. The resulting water is discharged as a further stream from the process. The organic phase from the phase separator can either be taken off at least partly as stream D1) or be subjected to a further work-up. The organic phase from the phase separator can be partly returned as runback to the column and/or be subjected to a further work-up by distillation. This preferably serves to remove water still comprised and/or undesirable organic components.

The bottom product obtained in the distillation in step d2) comprises the aromatics which have not been reacted or been reacted only insufficiently in the dealkylation, i.e. it is enriched in aromatics which have not been dealkylated or dealkylated to only a small extent. It can either be taken off directly as stream D2) or subjected to a further work-up. The bottom product obtained in the distillation in step d2) is preferably divided into at least two substreams. A first substream is preferably recirculated as absorption medium to step d) of the absorptive fractionation of the discharge from the dealkylation zone. For this purpose, this substream is, if necessary, cooled to a suitable temperature. A second substream is taken off as stream D2). The stream D2) can be subjected to removal of constituents which do not belong to the stream D2 before the recirculation to the dealkylation zone of step d). This is advantageous when, for example, an absorption solvent which is not obtained as intermediate in the process of the invention is used. In addition, it is advantageous to take off another purge stream at this point from stream D2) and, for example, pass it to a combustion apparatus in order to reduce the accumulation of components which do not react or react slowly under the conditions of the dealkylation.

Before being fed into the dealkylation, the stream D2) is preferably subjected to vaporization. A preferred variant is shown in FIG. 1 and explained in the associated description of the FIGURE.

In a specific embodiment, the stream D3) obtained in step d), which is depleted in aromatics and enriched in volatile by-products, is at least partly used for producing synthesis gas. If, according to the above-described preferred embodiment of the process of the invention, the fractionation of the discharge from the dealkylation zone in step d) comprises an absorption, the gas stream leaving the absorption apparatus (stream D3) can, optionally after a purification step to remove absorption medium and/or aromatics, be used at least partly for producing synthesis gas.

The stream D3) obtained in step d) can, in addition to the production of synthesis gas, be partly passed to various other uses. These include combustion. If the process of the invention is in the proximity of a pulp process, it can be advantageous to feed stream D3) into an apparatus of the pulp process. The stream D3) is particularly preferably fed to the waste liquor combustion (recovery boiler). This embodiment has the advantage that no additional apparatuses are required for steam or power generation or flue gas desulfurization in the case of combustion of the stream D3). In another variant, the combustion of stream D3) is preceded by desulfurization, e.g. in the form of a gas scrub to remove hydrogen sulfide, followed by conversion of the $H_2S$ formed into elemental sulfur. The formation of sulfur can be carried out by known methods, e.g. the Claus process. The combustion can instead also be followed by a desulfurization unit.

For synthesis gas production, at least one further stream comprising, for example, water vapor and/or oxygen can optionally be used in addition to stream E3).

In a specific embodiment of the process of the invention, the aromatics-depleted fraction C2) isolated in step c) is at least partly used for producing synthesis gas. It is also possible to use an offgas stream from the decomposition in step b) and/or the optional dealkylation in step d) in the production of synthesis gas. This offgas stream can be, for example, a burning-off gas from the combustion of relatively nonvolatile components. The introduction of such an offgas stream enables the $H_2/CO$ ratio of the synthesis gas to be reduced.

The production of synthesis gas preferably comprises the following steps:
a reforming step,
a converting step (in which additional water is introduced if required) in which the water gas shift reaction ($CO+H_2O \leftrightarrow H_2+CO_2$) proceeds,
optionally a step for the partial removal of acidic gases such as $CO_2$.

The production of synthesis gas is carried out according to the prior art, as is described, for example, in Ullmann's Encyclopedia of Industrial Chemistry, article "Gas Production", DOI: 10.1002/14356007.a12_169.pub2.

In a preferred variant, the synthesis gas produced in the process of the invention is (if necessary after further purification steps known per se for the removal of water, sulfur-comprising components, $CO_2$, etc.) used entirely or in part in at least one process which consumes hydrogen, CO or mixtures of the two. Such processes include, for example, hydrogenation, hydroformylation, carbonylation, synthesis of methanol, synthesis of hydrocarbons by the Fischer-Tropsch process, etc.

In a preferred embodiment of the process of the invention, a synthesis gas-comprising stream produced in the process or a hydrogen-enriched stream produced from the synthesis gas is fed to the decomposition in step b) and/or the optional dealkylation in step d). Enrichment of the synthesis gas with hydrogen can be effected, as described above, by means of the water gas shift reaction.

Preference is given to feeding a synthesis gas-comprising stream produced in the process or a hydrogen-enriched stream produced from the synthesis gas into the dealkylation in step d). The particular advantage of this variant is that the proportion of phenol(s) in the products of the dealkylation is higher than in the case of pure steam dealkylation, i.e. without introduction of hydrogen. The higher phenol formation represents an important advantage of the preparation of polyisocyanate according to the invention.

Amination (Step e)

The oxyaromatics composition obtained from the biomass starting material by decomposition and optionally further reaction and/or work-up steps is subjected to amination in step g). Here, the oxyaromatics composition is preferably reacted with an ammonia source in an amination zone to give the corresponding aromatic amines.

In step e), preference is given to subjecting the decomposition product from step b) or the aromatics-enriched fraction C1) from step c) or the discharge from the dealkylation zone in step d) or the stream D1) enriched in dealkylated aromatics from step d) to amination by reaction with an ammonia source.

The reaction with an ammonia source can be carried out by customary processes known to those skilled in the art, as are described, for example, in DE-B-1 289 530, U.S. Pat. No. 3,578,714, U.S. Pat. No. 5,214,210 and EP-A-0 321 275. The disclosure of these documents is hereby fully incorporated by reference.

The amination can be carried out using ammonia or an ammonia source which is capable of forming ammonia under the reaction conditions. Such ammonia sources include, for example, compounds which form ammonia on thermal decomposition, e.g. ammonium carbonate and ammonium sulfate. As an alternative, an organic amine which is preferably selected from among methylamine, ethylamine, n-propylamine, dimethylamine, diethylamine, dipropylamine, methylethylamine, cyclohexylamine, aminopyridines, aniline, methylaniline, ethylaniline, n-propylaniline, isopropylaniline, dimethylaniline, diethylaniline, dipropylaniline, methylethylaniline and methylpropylaniline can be used for the amination. Preference is given to using ammonia for the amination.

The amination is preferably carried out in the presence of a suitable catalyst. Preference is given to using a catalyst based on at least one Al oxide or Si—Al oxide.

If necessary, the starting materials can be subjected to preheating, which may be associated with vaporization, before the amination.

The temperature in the amination zone is preferably in the range from 100 to 600° C., particularly preferably from 200 to 450° C.

The absolute pressure in the amination zone is preferably in the range from 1 to 100 bar, particularly preferably from 1 to 30 bar.

As reactors for the amination, preference is given to using fixed beds or fluidized beds.

The molar ratio of ammonia to oxyaromatics in the amination is preferably in the range from 5:1 to 30:1.

The gas leaving the amination zone preferably comprises a greater molar proportion of amines than of oxyaromatics.

To work up the discharge taken from the amination zone, this discharge is preferably subjected to fractionation. The discharge from the amination zone is generally taken off in gaseous form. In a preferred embodiment, the discharge taken from the amination zone is cooled and fed to a first distillation column in order to separate off excess ammonia. This is preferably recirculated to the amination zone. The amines formed are obtained as a mixture with water and optionally small amounts of by-products at the bottom of the first distillation column. The bottom product from the first distillation column is fed to a second distillation column in order to separate off the water. The further fractionation is preferably effected in at least one further distillation column. Here, at least one stream E1) enriched in aromatic amines and at least one oxyaromatics-enriched stream E2) are obtained. Utilization of the technology of divided columns also makes it possible to combine a plurality of columns in one column provided with one or more side offtakes. Suitable columns having side offtakes, which in a specific embodiment are thermally coupled, and dividing wall columns are known to those skilled in the art.

The stream E1) enriched in aromatic amines is fed to the phosgenation (step g). The oxyaromatics-enriched stream E2) is preferably recirculated to the amination zone.

If desired, the stream E1) enriched in aromatic amines can be subjected to a further fractionation. A further fractionation is, in a specific embodiment, carried out when the stream E1) enriched in aromatic amines comprises monoamines (i.e. amines having one $NH_2$ group) and polyamines (i.e. amines having more than one $NH_2$ group, e.g. two, three or four $NH_2$ groups). The further fractionation is preferably carried out by distillation. A stream E1m) enriched in aromatic monoamines and a stream E1p) enriched in aromatic polyamines are then preferably obtained. In a specific embodiment, the stream E1m) enriched in aromatic monoamines is subjected to condensation with a formaldehyde source in step f) before the phosgenation in step g). The stream E1p) enriched in aromatic polyamines can either be subjected to condensation with a formaldehyde source in step f) before the phosgenation in step g) or be used directly for the phosgenation in step g).

In a specific embodiment, at least one amine which has not been obtained from biomass (hereinafter "conventional amines") is added to the amination product from step e) before the reaction in step f) and/or g). As indicated above, the term "biomass" refers, for the purposes of the invention, to plant material of nonfossil origin. The amines added preferably come from a fossil raw material source selected from among coal, petroleum, natural gas and upgrading products thereof, e.g. coke.

The amines used for the reaction in step f) and/or g) preferably comprise at least 50% by weight, particularly preferably at least 75% by weight, in particular at least 90% by weight, especially at least 99% by weight, of amines prepared according to the invention from a biomass starting material, based on the total amount of the amines used for the reaction in step f) and/or g).

conventional amines

Suitable conventional aromatic amines can be prepared from the corresponding aromatics such as benzene or toluene by processes known from the prior art. These include, in particular, nitration with subsequent hydrogenation of the nitro group to form the corresponding amine. Nitroaromatics can be prepared by batch or continuous processes. The nitrating agent is preferably either a mixture of nitric acid and sulfuric acid or nitric acid alone. Suitable processes for continuous preparation in the liquid phase are described, for example, by Meissner et al., Continuous production of nitrotoluenes, Ind. Eng. Chem., 46 4 (1954), 718-24 and in U.S. Pat. No. 2,773,911. Nitration using nitric acid alone is described in U.S. Pat. No. 2,739,174 and the gas-phase nitration of hydrocarbons is described in GB 586732. A summary of a suitable industrial process may be found, for example, in Leslie A. Carmichael, Aromatic Amines, SRI Stanford Research Institute, 1972. EP-A-748 788 and EP-A-059 7361 describe adiabatic and continuous liquid-phase nitration to produce nitrotoluene. U.S. Pat. No. 5,302,763 describes sulfuric acid-free nitration using nitric acid. EP-A-1 350 787 describes a process for the heterogeneously catalyzed nitration of toluene over acidic zeolites in order to increase the selectivity. EP-A-0 184 569 describes a process for heterogeneously catalyzed nitration in the gas phase over mixed oxides. A review of the preparation of dinitrotoluene may be found in Hermann et al., Industrial nitration of toluene to dinitrotoluene, ACS Symp. Series 623 (nitration), 234-249. EP-A-1 880 989 describes fine-chemicals embodiments of the process. Carrying out the process isothermally in the liquid phase is described in WO 2005/075407 and EP-A-0 903 336. Details of the wastewater treatment are described in DE 10329303 and integration into a wider integrated process is described in EP-A-1 132 347 and EP-A-0 976 718. CN 1854114 teaches nitration with addition of metal salts. The importance of concentrating the used sulfuric acid is described in DE-A-4230099. The information regarding dinitrotoluene as precursor of TDI applies analogously to mononitrobenzene as precursor of MDA/MDI. Descriptions of suitable continuous processes in the liquid phase may be found in U.S. Pat. No. 2,849,497 and U.S. Pat. No. 2,773,911. Possible reactors are, for example, stirred vessels having heat exchangers or flow tubes. Carrying out the reaction adiabatically in a flow tube is described in BE 724918, DE 4428460 and DE 4428461. Here, the nitrating acid takes up the heat of reaction of the nitration reaction. The heat stored in this way can be utilized to separate the by-product water from the reaction mixture by depressurization. A particular embodiment of an adiabatic flow tube for carrying out the nitration reaction of aromatics in the liquid phase may be found in DE 10223483, EP 0 489 211 and WO 01/64333. The adiabatic reaction in the liquid phase is particularly preferred in the preparation of mononitrobenzene compared to that of nitrotoluene since selectivities in respect of the formation of isomers do not have to be taken into account. Safe monitoring and carrying out of nitration processes is described in EP-A-1 445 246. Quadros et al., Ind. Eng. Chem. Res. 2004, 43, 4438-4445, are concerned with wastewater problems. The disclosure of the abovementioned documents is hereby fully incorporated by reference.

The aromatic nitrocompounds obtained by nitration are converted by hydrogenation into the corresponding amines. Water is obtained as by-product of the hydrogenation. The hydrogenation is preferably carried out in the presence of a catalyst. It can be carried out industrially in a wide variety of industrial embodiments such as fluidized beds or fixed beds or in the liquid or gaseous phase. The high heat of reaction is advantageously utilized for generation of energy and/or integrated into an integrated heat system (see EP-A-1 137 623, U.S. Pat. No. 7,064,237, EP-A-0 696 573, EP-A-0 748 789). Carrying out the reaction in coated microchannels is described in DE-A-10 2006 011 497. The disclosure of the abovementioned document is hereby fully incorporated by reference.

Ring hydrogenation

The amination product obtained in step e) (especially the stream E1p enriched in aromatic polyamines) can be subjected to ring hydrogenation before an optional condensation with a formaldehyde source in step f) or before the phosgenation in step g). Economically and ecologically advantageous aliphatic polyisocyanates can be obtained in this way. Suitable ring hydrogenation processes are described, for example, in U.S. Pat. No. 6,429,338, WO 2006/066762 and EP-A-799 817. The disclosure of these documents is hereby fully incorporated by reference.

Condensation with a Formaldehyde Source (Step f)

To obtain polyisocyanates having high NCO numbers, the amination product obtained in step e) can be partly or fully subjected to condensation with formaldehyde before the phosgenation in step g). Furthermore, it is possible to mix condensed amines with uncondensed amines for the phosgenation in step g).

As regards suitable processes for the condensation of the aromatic amines with formaldehyde, DE-A-19961973, DD 295628 and DD 238042 are incorporated by reference.

Suitable formaldehyde sources for the reaction in step f) are formalin solutions, formaldehyde oligomers, e.g. trioxane, and polymers of formaldehyde, e.g. paraformaldehyde. Preference is given to using paraformaldehyde or formalin solution. It is of course also possible to use gaseous formaldehyde.

The molar ratio of the amines used to formaldehyde is preferably from 1.5:1 to 10:1, in particular from 2:1 to 6:1.

The condensation reaction is preferably carried out with addition of acidic catalysts. As acidic catalysts, it is possible to use the catalysts which are generally known for this reaction, for example mineral acids such as phosphoric acid, sulfuric acid and hydrochloric acid. Hydrochloric acid is preferably used as catalyst for the condensation in step f).

The molar ratio of catalyst to amines is preferably from 0.01 to 1, in particular from 0.1 to 0.5.

The condensation reaction is usually carried out at temperatures of from 20 to 150° C., preferably from 20 to 130° C. In a preferred variant, aniline and the acidic catalyst are initially charged and formaldehyde is added.

The acidic amine mixture from the condensation can be worked up by conventional methods such as neutralization, phase separation and distillation.

Phosgenation (Step g)

The phosgenation of the amine product obtained in step e) (especially the stream E1p enriched in aromatic polyamines) or the condensation product obtained in step f) can be carried out by conventional methods known to those skilled in the art.

Liquid-phase phosgenations which are suitable for the phosgenation in step g) are described, for example, in EP-A-1 616 857, WO 2004/056756, WO 2006/130405, EP-A-1 509 496, EP-A-1 270 544 and DE-A-199 61 973. The disclosure of these documents is hereby fully incorporated by reference.

As an alternative, the phosgenation in step g) can be carried out as a gas-phase phosgenation. An advantage of phosgenation in the gas phase at high temperatures is that the formation of undesirable intermediates of the amine hydrochlorides can generally be avoided. Such processes are described in EP-A-593 334, WO 2003/045900, WO 2008/086922 and WO 2008/006775 (aerosol phosgenation), which are hereby likewise incorporated by reference.

Furthermore, the phosgenation in step g) can be carried out in supercritical solvents (WO 2008/049783). The isocyanates themselves (EP-A-1 401 802, U.S. Pat. No. 6,683,204) or ionic liquids (WO 2006/048141 BASF, WO 2006/048171 BASF) can also be used as solvents.

In a suitable embodiment, the phosgenation in step g) is carried out in a solvent which is inert under the phosgenation conditions. Suitable solvents are, for example, aromatics such as toluene, monochlorobenzene or dichlorobenzene. The phosgenation in step g) can be carried out in conventional reactors, for example stirred vessels or columns.

The temperature in the phosgenation is preferably in the range from 50 to 150° C., particularly preferably from 70 to 100° C.

The pressure in the phosgenation is preferably in the range from 0.5 to 10 bar, particularly preferably from 0.8 to 5 bar.

The crude isocyanate obtained in the phosgenation in step g) can be purified by conventional methods, for example distillation. Apparatuses which can be used for this purpose are falling film evaporators or thin film evaporators or packed columns. This purification can be carried out in two process steps. Firstly, phosgene, HCl and solvents are separated off from the crude isocyanate by stripping at a temperature of from 50 to 150° C., optionally under reduced pressure or by introduction of inert gas. The remaining solvent and possibly chlorine-comprising compounds are subsequently removed at a temperature of from 150 to 190° C., again by stripping or under reduced pressure.

The invention claimed is:

1. A process for preparing a polyisocyanate, the process comprising:
    phosgenating a composition comprising aromatic amines having a $C^{14}$ to $C^{12}$ isotope ratio in the range from $0.5 \times 10^{-12}$ to $5 \times 10^{-12}$,
    wherein the composition comprising aromatic amines is prepared from a biomass starting material by decomposing the biomass starting material, to obtain an oxyaromatic composition comprising an aromatic comprising at least one selected from the group consisting of a hydroxy group and an alkoxy group per molecule; and
    aminating the oxyaromatic composition, to obtain an amination product,
    wherein the composition in the phosgenating is the amination product.

2. The process of claim 1,
    wherein the oxyaromatic composition comprises, based on a total weight, at least 75% by weight of a monocyclic aromatic.

3. The process of claim 1, further comprising, but prior to the phosgenating:
    (I) decomposing the biomass starting material, to obtain an oxyaromatic composition comprising an aromatic comprising at least one selected from the group consisting of a-hydroxy group and an alkoxy group per molecule;
    (II) animating the oxyaromatic composition, to obtain an amination product; and
    (III) condensating the amination product with a formaldehyde source, to obtain a condensation product,
    wherein the composition in the phosgenating is the condensation product.

4. The process of claim 1, further comprising, prior to the phosgenating:
    a) decomposing the biomass starting material, to obtain a decomposition product;
    b) optionally separating the decomposition product into an aromatics-enriched fraction B1) and an aromatics-depleted fraction B2);
    c) optionally feeding the decomposition product or the aromatics-enriched fraction B1) into a dealkylation zone and reacting the decomposition product or the aromatics-enriched fraction B1) in the presence of at least one selected from the group consisting of hydrogen and water vapor,
    taking a discharge from the dealkylation zone, and
    optionally separating the discharge, to obtain a stream C1) enriched in dealkylated aromatics and a stream C2) enriched in more volatile components;
    d) aminating the decomposition product, the aromatics-enriched fraction B1), the discharge from the dealkylation zone, or the stream C1) with an ammonia source in an amination zone, to obtain an amination product; and
    e) optionally condensing the amination product with a formaldehyde source, to obtain a condensation product,
    wherein the compound in the phosgenating is the amination product or the condensation product.

5. The process of claim 1,
wherein the biomass starting material is a lignin-comprising material.

6. The process of claim 1,
wherein the biomass starting material is a lignocellulose material or a digestion product of a lignocellulose material.

7. The process of claim 1,
wherein the biomass starting material is a lignin-comprising stream from the digestion of a lignocellulose material for producing cellulose.

8. The process of claim 1,
wherein the decomposing comprises pyrolyzing the biomass starting material.

9. The process of claim 8,
wherein the pyrolyzing is not carried out with addition of a hydrogen compound.

10. The process of claim 8,
wherein the pyrolyzing is carried out with addition of hydrogen.

11. The process of claim 8,
wherein the biomass starting material comprises a black liquor material having a liquid content of not more than 70% by weight at 20° C., 1013 mbar, based on a total weight of the black liquor material.

12. The process of claim 1,
wherein the decomposing is carried out in a liquid phase.

13. The process of claim 12,
wherein the decomposing is carried out in the presence of an aqueous-alkaline, aqueous-acidic, or organic decomposition medium.

14. The process of claim 13,
wherein the biomass starting material in the decomposing comprises a cellulose-depleted fraction from a pulp process.

15. The process of claim 4,
wherein the separating b) is performed and is carried out by at least one selected from the group consisting of a distillation, extraction, absorption, and membrane process.

16. The process of claim 4,
wherein the decomposing a) comprises pyrolyzing the biomass starting material and
the separating b) is performed and comprises an absorption.

17. The process of claim 4,
wherein the decomposing a) is carried out in a liquid phase and
the separating b) is performed and comprises at least one selected from the group consisting of an extraction and a distillation.

18. The process of claim 17,
wherein the separating b) is performed and comprises:
b1) extracting the decomposition product, to obtain an aromatics-enriched extract and an aromatics-depleted residue;
b2) optionally separating the extract into a fraction enriched in extractant and depleted in aromatics and a fraction enriched in aromatics and depleted in extractant; and
b3) adding the aromatics-enriched extract of b1) or the aromatics-enriched fraction of b2) into at least one selected from the group consisting of the separating c) and the aminating d).

19. The process of claim 4,
wherein a reaction in c) comprises at least one selected from the group consisting of a hydrodealkylation and a steam dealkylation.

20. The process of claim 4,
wherein a temperature in the dealkylation zone is in a range from 400 to 900° C.

21. The process of claim 4,
wherein an absolute pressure in the dealkylation zone is in a range from 1 to 100 bar.

22. The process of claim 4,
wherein the discharge from the dealkylation zone in c) is subjected to a fractionation to obtain the following three streams:
C1) a stream enriched in monocyclic oxyaromatics which are unalkylated or have a low degree of alkylation;
C2) a stream enriched in aromatics which are not dealkylated or are dealkylated to only a small extent; and
C3) a stream enriched in by-products which are more volatile than C1) and C2).

23. The process of claim 4,
wherein the aminating is carried out with ammonia.

24. The process of claim 4, wherein the discharge from the amination zone in d) is subjected to a fractionation to obtain a stream D1) enriched in aromatic amines and an oxyaromatics-enriched stream D2).

25. The process of claim 24, wherein the fractionation comprises:
d1) fractional distillation of the discharge from the amination zone, to obtain an ammonia-enriched fraction and an ammonia-depleted fraction;
d2) optionally separating water from the ammonia-depleted fraction by distillation; and
d3) fractional distillation, to obtain the stream D1) enriched in aromatic amines and the oxyaromatics-enriched stream D2).

26. The process of claim 24, further comprising:
at least partially condensating the stream D1) with a formaldehyde source.

27. The process of claim 24, wherein the stream D1) is at least partly employed without prior condensation with a formaldehyde source in the phosgenating.

28. The process of claim 24, further comprising:
further fractionation of the stream D1), to obtain a stream D1m) enriched in aromatic monoamines and a stream D1p) enriched in aromatic polyamines.

29. The process of claim 28, comprising:
condensing the stream D1m) with a formaldehyde source in e) before the phosgenating.

30. The process of claim 28, comprising condensing the stream D1p) with a formaldehyde source in e) before the phosgenating or directly phosgenating the stream D1p).

31. The process of claim 24, wherein the oxyaromatics-enriched stream D2) is recirculated to the amination zone in d).

32. The process of claim 4, further comprising:
adding an amine which has not been obtained from biomass to the amination product of d) before the reaction in at least one selected from the group consisting of the condensing and the phosgenating.

* * * * *